US005792845A

United States Patent [19]

O'Reilly et al.

[11] Patent Number: 5,792,845

[45] Date of Patent: Aug. 11, 1998

[54] NUCLEOTIDES ENCODING ANGIOSTATIN PROTEIN AND METHOD OF USE

[75] Inventors: Michael S. O'Reilly, Winchester; M. Judah Folkman, Brookline, both of Mass.

[73] Assignee: The Children's Medical Center Corporation, Boston, Mass.

[21] Appl. No.: 326,785

[22] Filed: Oct. 20, 1994

Related U.S. Application Data

[63] Continuation-in-part of Ser. No. 248,629, Apr. 26, 1994, Pat. No. 5,639,725.

[51] Int. Cl.[6] .......................... C07H 21/04; C12N 15/00; C07K 14/00

[52] U.S. Cl. .................... 536/23.1; 536/23.5; 435/172.3; 435/320.1; 530/350

[58] Field of Search .................................... 530/350, 380; 424/94.63; 435/212, 226; 514/12; 536/23.1 T, 23.1

[56] References Cited

FOREIGN PATENT DOCUMENTS

91/10424 7/1991 WIPO .
WO 91/10424 7/1991 WIPO .

OTHER PUBLICATIONS

Derwent Publications, Ltd., London; JP 58–036–391 (Sankyo KK) Mar. 3, 1983 (Abstract).

M. O'Reilly et al., "The Suppression of Tumor Metastases by a Primary Tumor" *Science* vol. 44, pp. 474–476; 1993.

T. E. Maione et al., "Inhibition of Angiogenesis by Recombinant Human Platelet Factor–4 and Related Peptides" *Science* vol. 247, pp. 77–79; Jan. 5,1990.

M. A. Moses et al., "Identification of an Inhibitor of Neovascularization from Cartilage" *Science* vol. 248, pp. 1408–1410; Jun. 15, 1990.

Folkman J., Tumor angiogenesis: Therapeutic implications., *N. Engl. Jour. Med.* 285:1182 1186, 1971.

Algire GH, et al. Vascular reactions of normal and malignant tumors in vivo. I. Vascular reactions of mice to wounds and to normal and neoplastic transplants. *J. Natl. Cancer Inst.* 6:73–85, 1945.

Folkman J, et al., Tumor behavior in isolated perfused organs: In vitro growth and metastasis of biopsy material in rabbit thyroid and canine intestinal segments. *Annals of Surgery* 164:491–502, 1966.

Gimbrone, M.A., Jr. et al., Tumor growth and neovascularization: An experimental model using the rabbit cornea. *J. Natl. Cancer Institute* 52:41–427, 1974.

Gimbrone MA Jr., et al., Tumor dormancy in vivo by prevention of neovascularization. *J. Exp. Med.* 136:261–276.

Knighton D., Avascular and vascular phases of tumor growth in the chick embryo. *British J. Cancer,* 35:347–356, 1977.

Lien W., et al., The blood supply of experimental liver metastases. II. A microcirculatory study of normal and tumor vessels of the liver with the use of perfused silicone rubber. *Surgery* 68:334–340, 1970.

Folkman J, et al., Induction of angiogenesis during the transition from hyperplasia to neoplasia. *Nature* 339:58–61, 1989.

Kim K J, et al., Inhibition of vascular endothelial growth factor–induced angiogenesis suppresses tumor growth in vivo. *Nature* 362:841–844, 1993.

Hori A, et al., Suppression of solid tumor growth by immunoneutralizing monoclonal antibody against human basic fibroblast growth factor. *Cancer Research,* 51:6180–6184, 1991.

Gross JL, et al. Modulation of solid tumor growth in vivo by bFGF. *Proc. Amer. Assoc. Canc. Res.* 31:79, 1990.

Ingber D, et al., Angioinhibins: Synthetic analogues of fumagillin which inhibit angiogenesis and suppress tumor growth. *Nature,* 48:555–557, 1990.

Weidner N, et al., Tumor angiogenesis and metastasis—correlation in invasive breast carcinoma. *N. Engl. J. Med.* 324:1–8, 1991.

Weidner N, et al., Tumor angiogenesis: A new significant and independent prognostic indicator in early–stage breast carcinoma, *J Natl. Cancer Inst.* 84:1875–1887, 1992.

Weidner N, Carroll PR, Flax J, Blumenfeld W, Folkman J. Tumor angiogenesis correlates with metastasis in invasive prostate carcinoma. *American Journal of Pathology,* 143(2):401–409, 1993.

Srivastava A, et al. The prognostic significance of tumor vascularity in intermediate thickness (0.76–4.0 mm thick) skin melanoma. *Amer. J. Pathol.* 133:419–423, 1988.

Nguyen M, et al., Elevated levels of an angiogenic peptide, basic fibroblast growth factor, in urine of bladder cancer patients. *J. Natl. Cancer Inst.* 85:241–242, 1993.

Robbins, K.C., "The plasminogen–plasmin enzyme system" *Hemostasis and Thrombosis, Basic Principles and Practice,* 2nd Edition, ed. by Colman, R.W. et al. J.B. Lippincott Company, pp. 340–357, 1987.

Yoshimura, T, et al., "Cloning, sequencing, and expression of human macrophage stimulating protein (MSP, MST1) confirms MSP as a member of the family of kringle proteins and locates the MSP gene on Chromosome 3" *J. Biol. Chem.,* vol. 268, No. 21, pp. 15461-15468, 1993.

(List continued on next page.)

*Primary Examiner*—Suzanne E. Ziska
*Attorney, Agent, or Firm*—Jones & Askew

[57] ABSTRACT

The present invention comprises an endothelial inhibitor and method of use therefor. The endothelial inhibitor is a protein isolated from the blood or urine that is eluted as a single peak from C4-reverse phase high performance liquid chromatography. The endothelial inhibitor is a molecule comprising a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of a murine plasminogen molecule.

26 Claims, 15 Drawing Sheets

OTHER PUBLICATIONS

Browne, M.J., et al., "Expression of recombinant human plasminogen and aglycoplasminogen in HeLa cells" Fibrinolysis vol. 5 (4). 257–260, 1991.

Brem et al., "Interstitial chemotherapy with drug polymer implants for treatment of recurrent gliomas," *J. Neurosurg.* 74:441–446 (1991).

Muthukkaruppan Vr., et al., Angiogenesis in the mouse cornea. *Science* 205:1416–1418, 1979.

Passaniti A, et al., "A simple, quantitative method for assessing angiogenesis and anti-angiogenic agents using reconstituted basement membrane, heparin and fibroblast growth factor," *Lab. Invest.*, vol. 67, p. 519 (1992).

Folkman J., Angiogenesis and its inhibitors in "*Important Advances in Oncology 1985*", VT DeVita, S. Hellman and S. Rosenberg, editors J.B. Lippincott, Philadelphia 1985.

Obeso, et al., "Methods in Laboratory Investigation, A Hemangioendothelioma-derived cell line; Its use as a Model for the Study of Endothelial Cell Biology," *Lab Invest.*, 63(2), pp. 259–269, 1990.

Sotrrup-Jensen, L., et al., *Progress in Chemical Fibrinolysis and Thrombolysis*, vol. 3, Davidson, J.F., et al. eds. Raven Press, New York, p. 191 (1978).

Browne, et al "Expression of Recombinant Human Plasminogen & Aglycoplasminogen in HeLa Cells", Fibrinolysis (1991), 5, 257–260.

Schaller, et al "Complete AA Sequence of Bovine Plasiminogen.", Eur J. Biochem (1985) 149; 267–278.

Sottrup-Jensen, et al "The Primary Structure of Human Plasminogen: Isolation of Two Lysine-Binding Fragments and One Mini Plasminogen (MW 38,000) by Elastase-Catalyzed-Specific Limited Proteolysis", Progr. in Ch Fibrinolysis & Thrombosis (1978) Raven Press, NY, vol. 3; 191–209.

Mouse Plasminogen Sequence:

met asp his lys glu val ile leu leu phe leu leu leu leu lys
pro gly gln gly asp ser leu asp gly tyr ile ser thr gln gly
ala ser leu phe ser leu thr lys lys gln leu ala ala gly gly
val ser asp cys leu ala lys cys glu gly glu thr asp phe val
cys arg ser phe gln tyr his ser lys glu gln gln cys val ile
met ala glu asn ser lys thr ser ser ile ile arg met arg asp
val ile leu phe glu lys arg val tyr leu ser glu cys lys thr
gly ile gly asn gly tyr arg gly thr met ser arg thr lys ser
gly val ala cys gln lys trp gly ala thr phe pro his val pro
asn tyr ser pro ser thr his pro asn glu gly leu glu glu asn
tyr cys arg asn pro asp asn asp glu gln gly pro trp cys tyr
thr thr asp pro asp lys arg tyr asp tyr cys asn ile pro glu
cys glu glu glu cys met tyr cys ser gly glu lys tyr glu gly
lys ile ser lys thr met ser gly leu asp cys gln ala trp asp
ser gln ser pro his ala his gly tyr ile pro ala lys phe pro
ser lys asn leu lys met asn tyr cys his asn pro asp gly glu
pro arg pro trp cys phe thr thr asp pro thr lys arg trp glu
tyr cys asp ile pro arg cys thr thr pro pro pro pro pro ser
pro thr tyr gln cys leu lys gly arg gly glu asn tyr arg gly
thr val ser val thr val ser gly lys thr cys gln arg trp ser
glu gln thr pro his arg his asn arg thr pro glu asn phe pro
cys lys asn leu glu glu asn tyr cys arg asn pro asp gly glu
thr ala pro trp cys tyr thr thr asp ser gln leu arg trp glu
tyr cys glu ile pro ser cys glu ser ser ala ser pro asp gln
ser asp ser ser val pro pro glu glu gln thr pro val val gln
glu cys tyr gln ser asp gly gln ser tyr arg gly thr ser ser
thr thr ile thr gly lys lys cys gln ser trp ala ala met phe
pro his arg his ser lys thr pro glu asn phe pro asp ala gly
leu glu met asn tyr cys arg asn pro asp gly asp lys gly pro
trp cys tyr thr thr asp pro ser val arg trp glu tyr cys asn
leu lys arg cys ser glu thr gly gly ser val val glu leu pro
thr val ser gln glu pro ser gly pro ser asp ser glu thr asp
cys met tyr gly asn gly lys asp tyr arg gly lys thr ala val
thr ala ala gly thr pro cys gln gly trp ala ala gln glu pro
his arg his ser ile phe thr pro gln thr asn pro arg ala asp
leu glu lys asn tyr cys arg asn pro asp gly asp val asn gly
pro trp cys tyr thr thr asn pro arg lys leu tyr asp tyr cys
asp ile pro leu cys ala ser ala ser ser phe glu cys gly lys
pro gln val glu pro lys lys cys pro gly arg val val gly gly
cys val ala asn pro his ser trp pro trp gln ile ser leu arg
thr arg phe thr gly gln his phe cys gly gly thr leu ile ala
pro glu trp val leu thr ala ala his cys leu glu lys ser ser
arg pro glu phe tyr lys val ile leu gly ala his glu glu tyr
ile arg gly leu asp val gln glu ile ser val ala lys leu ile
leu glu pro asn asn arg asp ile ala leu leu lys leu ser arg
pro ala thr ile thr asp lys val ile pro ala cys leu pro ser

Fig. 1A

| | | | | | | | | | | | | | | |
|---|---|---|---|---|---|---|---|---|---|---|---|---|---|---|
| pro | asn | tyr | met | val | ala | asp | arg | thr | ile | cys | tyr | ile | thr | gly |
| trp | gly | glu | thr | gln | gly | thr | phe | gly | ala | gly | arg | leu | lys | glu |
| ala | gln | leu | pro | val | ile | glu | asn | lys | val | cys | asn | arg | val | glu |
| tyr | leu | asn | asn | arg | val | lys | ser | thr | glu | leu | cys | ala | gly | gln |
| leu | ala | gly | gly | val | asp | ser | cys | gln | gly | asp | ser | gly | gly | pro |
| leu | val | cys | phe | glu | lys | asp | lys | tyr | ile | leu | gln | gly | val | thr |
| ser | trp | gly | leu | gly | cys | ala | arg | pro | asn | lys | pro | gly | val | tyr |
| val | arg | val | ser | arg | phe | val | asp | trp | ile | glu | arg | glu | met | arg |
| asn | asn | | | | | | | | | | | | | |

Fig. 1B

MOUSE
HUMAN
RHESUS MONKEY
PORCINE
BOVINE val tyr leu ser glu cys lys thr gly ile gly asn gly tyr arg gly
val tyr leu ser glu cys lys thr gly asn gly lys asn tyr arg gly
val tyr leu ser glu cys lys thr gly asn gly lys asn tyr arg gly
ile tyr leu ser glu cys lys thr gly asn gly lys asn tyr arg gly
ile tyr leu leu glu cys lys thr gly asn gly gln thr tyr arg gly thr met ser arg thr lys ser gly val ala cys gln lys trp gly ala
thr met ser lys thr lys asn gly ile thr cys gln lys trp ser ser
thr met ser lys thr arg thr gly ile thr cys gln lys trp ser ser
thr thr ser lys thr lys ser gly val ile cys gln lys trp ser val
thr thr ala glu thr lys ser gly val thr cys gln lys trp ser ala thr phe pro his val pro asn tyr ser pro ser thr his pro asn glu
thr ser pro his arg pro arg phe ser pro ala thr his pro ser glu
thr ser pro his arg pro thr phe ser pro ala thr his pro ser glu
ser ser pro his ile pro lys tyr ser pro glu lys phe pro leu ala
thr ser pro his val pro lys phe ser pro glu lys phe pro leu ala gly leu glu glu asn tyr cys arg asn pro asp asn asp glu gln gly
gly leu glu glu asn tyr cys arg asn pro asp asn asp pro gln gly
gly leu glu glu asn tyr cys arg asn pro asp asn asp gly gln gly
gly leu glu glu asn tyr cys arg asn pro asp asn asp glu lys gly
gly leu glu glu asn tyr cys arg asn pro asp asn asp glu asn gly pro trp cys tyr thr thr asp pro asp lys arg tyr asp tyr cys asn
pro trp cys tyr thr thr asp pro glu lys arg tyr asp tyr cys asp
pro trp cys tyr thr thr asp pro glu glu arg phe asp tyr cys asp
pro trp cys tyr thr thr asp pro glu thr arg phe asp tyr cys asp
pro trp cys tyr thr thr asp pro asp lys arg tyr asp tyr cys asp ile pro glu cys glu glu glu cys met tyr cys ser gly glu lys tyr
ile leu glu cys glu glu glu cys met his cys ser gly glu asn tyr
ile pro glu cys glu asp glu cys met his cys ser gly glu asn tyr
ile pro glu cys glu asp glu cys met his cys ser gly glu his tyr
ile pro glu cys glu asp lys cys met his cys ser gly glu asn tyr glu gly lys ile ser lys thr met ser gly leu asp cys gln ala trp
asp gly lys ile ser lys thr met ser gly leu glu cys gln ala trp
asp gly lys ile ser lys thr met ser gly leu glu cys gln ala trp
glu gly lys ile ser lys thr met ser gly ile glu cys gln ser trp
glu gly lys ile ala lys thr met ser gly arg asp cys gln ala trp

Fig. 2A asp ser gln ser pro his ala his gly tyr ile pro ala lys phe pro
asp ser gln ser pro his ala his gly tyr ile pro ser lys phe pro
asp ser gln ser pro his ala his gly tyr ile pro ser lys phe pro
gly ser gln ser pro his ala his gly tyr leu pro ser lys phe pro
asp ser gln ser pro his ala his gly tyr ile pro ser lys phe pro ser lys asn leu lys met asn tyr cys his asn pro asp gly glu pro
asn lys asn leu lys lys asn tyr cys arg asn pro asp arg glu leu
asn lys asn leu lys lys asn tyr cys arg asn pro asp gly glu pro
asn lys asn leu lys met asn tyr cys arg asn pro asp gly glu pro
asn lys asn leu lys met asn tyr cys arg asn pro asp gly glu pro arg pro trp cys phe thr thr asp pro thr lys arg trp glu tyr cys
arg pro trp cys phe thr thr asp pro asn lys arg trp glu leu cys
arg pro trp cys phe thr thr asp pro asn lys arg trp glu leu cys
arg pro trp cys phe thr thr asp pro asn lys arg trp glu phe cys
arg pro trp cys phe thr thr asp pro gln lys arg trp glu phe cys asp ile pro arg cys thr thr pro pro pro pro pro ser pro thr tyr
asp ile pro arg cys thr thr pro pro pro ser ser gly pro thr tyr
asp ile pro arg cys thr thr pro pro pro ser ser gly pro thr tyr
asp ile pro arg cys thr thr pro pro pro thr ser gly pro thr tyr
asp ile pro arg cys thr thr pro pro pro ser ser gly pro lys tyr gln cys leu lys gly arg gly glu asn tyr arg gly thr val ser val
gln cys leu lys gly thr gly glu asn tyr arg gly asn val ala val
gln cys leu lys gly thr gly glu asn tyr arg gly asp val ala val
gln cys leu lys gly arg gly glu asn tyr arg gly thr val ser val
gln cys leu lys gly thr gly lys asn tyr gly gly thr val ala val thr val ser gly lys thr cys gln arg trp ser glu gln thr pro his
thr val ser gly his thr cys gln his trp ser ala gln thr pro his
thr val ser gly his thr cys his gly trp ser ala gln thr pro his
thr ala ser gly his thr cys gln arg trp ser ala gln ser pro his
thr glu ser gly his thr cys gln arg trp ser glu gln thr pro his arg his asn arg thr pro glu asn phe pro cys lys asn leu glu glu
thr his asn arg thr pro glu asn phe pro cys lys asn leu asp glu
thr his asn arg thr pro glu asn phe pro cys lys asn leu asp glu
lys his asn arg thr pro glu asn phe pro cys lys asn leu glu glu
lys his asn arg thr pro glu asn phe pro cys lys asn leu glu glu asn tyr cys arg asn pro asp gly glu thr ala pro trp cys tyr thr
asn tyr cys arg asn pro asp gly lys arg ala pro trp cys his thr
asn tyr cys arg asn pro asp gly glu lys ala pro trp cys tyr thr
asn tyr cys arg asn pro asp gly glu thr ala pro trp cys tyr thr
asn tyr cys arg asn pro asp gly glu lys ala pro trp cys tyr thr

Fig. 2B thr asp ser gln leu arg trp glu tyr cys glu ile pro ser cys glu
thr asn ser gln val arg trp glu tyr cys lys ile pro ser cys asp
thr asn ser gln val arg trp glu tyr cys lys ile pro ser cys glu
thr asp ser glu val arg trp asp tyr cys lys ile pro ser cys gly
thr asn ser glu val arg trp glu tyr cys thr ile pro ser cys glu ser ser ala ser pro asp gln ser asp ser ser val pro pro glu glu
ser ser pro val ser thr glu gln leu ala pro thr ala pro pro glu
ser ser pro val ser thr glu pro leu asp pro thr ala pro pro glu
ser ser thr thr ser thr glu his leu asp ala pro val pro pro glu
ser ser pro leu ser thr glu arg met asp val pro val pro pro glu gln thr pro val val gln glu cys tyr gln ser asp gly gln ser tyr
leu thr pro val val gln asp cys tyr his gly asp gly gln ser tyr
leu thr pro val val gln glu cys tyr his gly asp gly gln ser tyr
gln thr pro val ala gln asp cys tyr arg gly asn gly glu ser tyr
gln thr pro val pro gln asp cys tyr his gly asn gly gln ser tyr arg gly thr ser ser thr thr ile thr gly lys lys cys gln ser trp
arg gly thr ser ser thr thr thr thr gly lys lys cys gln ser trp
arg gly thr ser ser thr thr thr thr gly lys lys cys gln ser trp
arg gly thr ser ser thr thr ile thr gly arg lys cys gln ser trp
arg gly thr ser ser thr thr ile thr gly arg lys cys gln ser trp ala ala met phe pro his arg his ser lys thr pro glu asn phe pro
ser ser met thr pro his arg his gln lys thr pro glu asn tyr pro
ser ser met thr pro his trp his glu lys thr pro glu asn phe pro
val ser met thr pro his arg his glu lys thr pro gly asn phe pro
ser ser met thr pro his arg his leu lys thr pro glu asn tyr pro asp ala gly leu glu met asn tyr cys arg asn pro asp gly asp lys
asn ala gly leu thr met asn tyr cys arg asn pro asp ala asp lys
asn ala gly leu thr met asn tyr cys arg asn pro asp ala asp lys
asn ala gly leu thr met asn tyr cys arg asn pro asp ala asp lys
asn ala gly leu thr met asn tyr cys arg asn pro asp ala asp lys gly pro trp
gly pro trp
gly pro trp
ser pro trp
ser pro trp

Fig. 2C

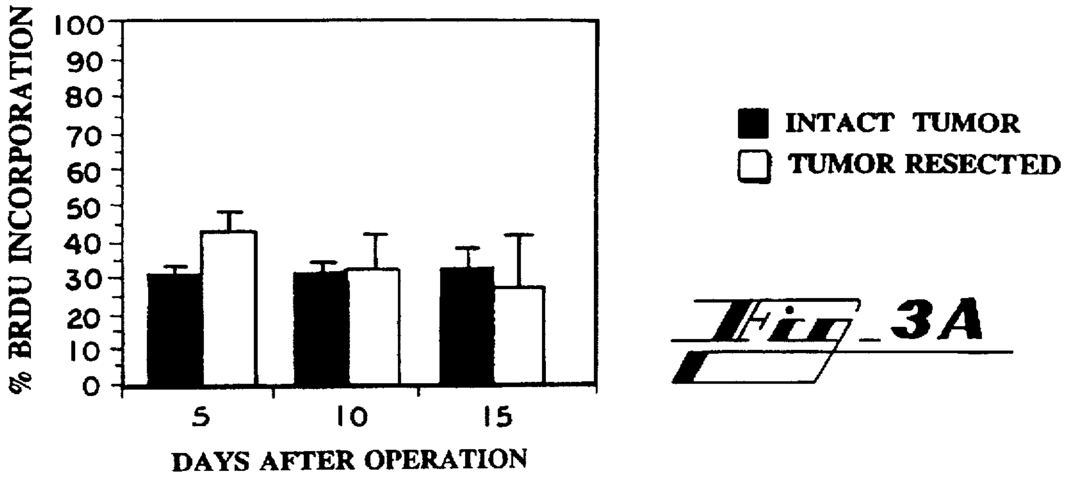
Fig_3A
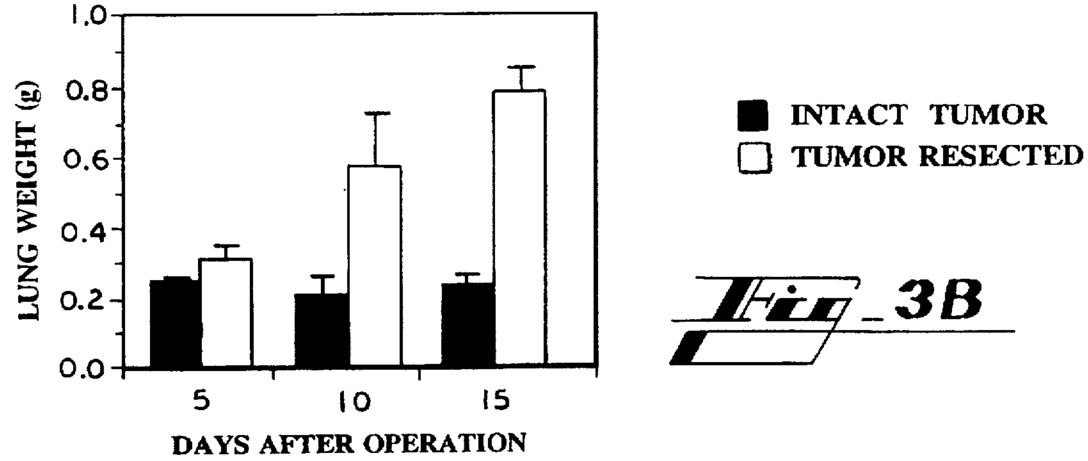
Fig_3B
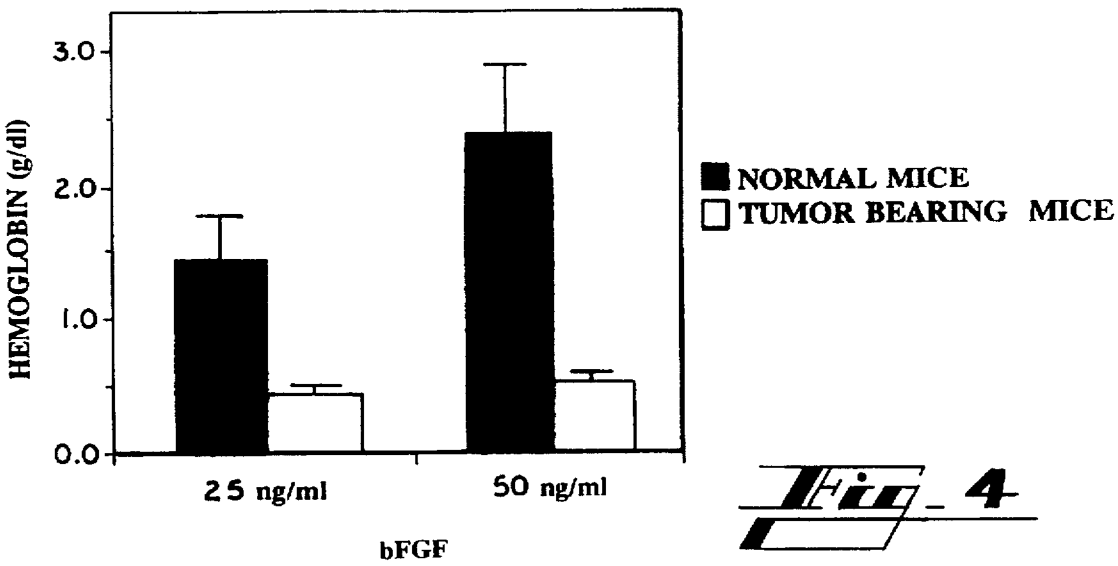
Fig_4

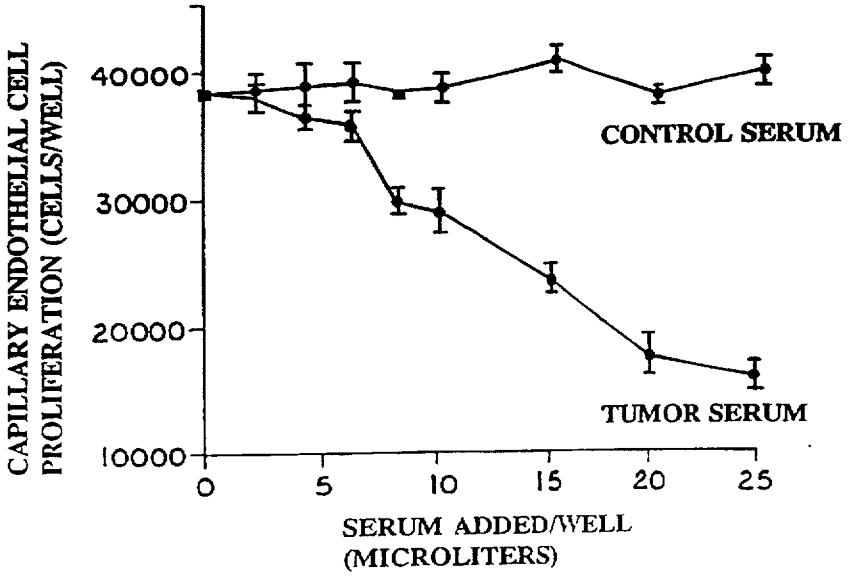
FIG. 5
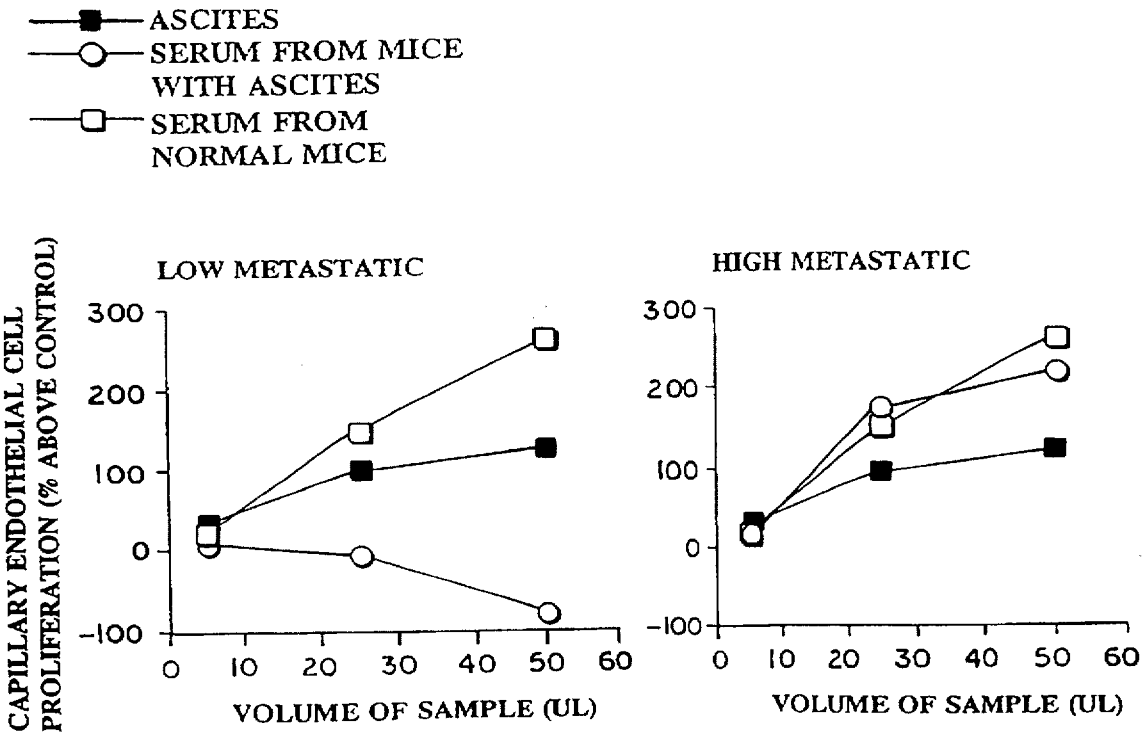
FIG. 6A
FIG. 6B

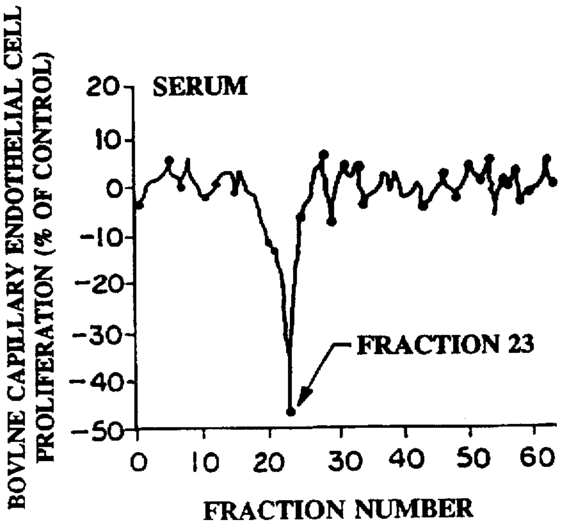
Fig_7A
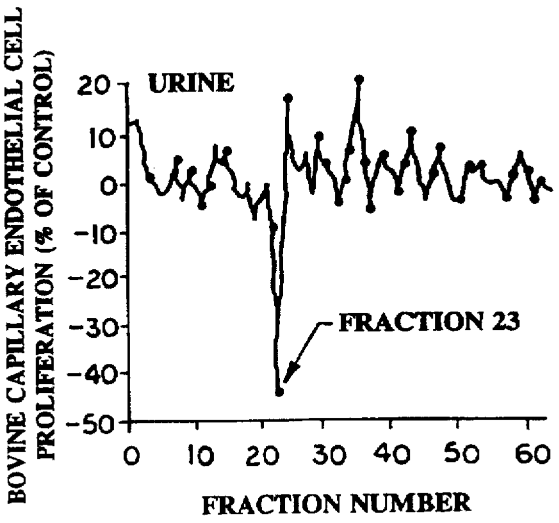
Fig_7B

Fig_ 11

TREATMENT OF LLC-LM PRIMARY TUMORS WITH ANGIOSTATIN
(80 mg/kg/day)

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 812
( B ) TYPE: amino acid
( D ) TOPOLOGY: linear ( x i ) SEQUENCE DESCRIPTION: SEQ ID NO: 1:

Met Asp His Lys Glu Val Ile Leu Leu Phe Leu Leu Leu Leu Lys
1 5 10 15

Pro Gly Gln Gly Asp Ser Leu Asp Gly Tyr Ile Ser Thr Gln Gly
20 25 30

Ala Ser Leu Phe Ser Leu Thr Lys Lys Gln Leu Ala Ala Gly Gly
35 40 45

Val Ser Asp Cys Leu Ala Lys Cys Glu Gly Glu Thr Asp Phe Val
50 55 60

Cys Arg Ser Phe Gln Tyr His Ser Lys Glu Gln Gln Cys Val Ile
65 70 75

Met Ala Glu Asn Ser Lys Thr Ser Ser Ile Ile Arg Met Arg Asp
80 85 90

Val Ile Leu Phe Glu Lys Arg Val Tyr Leu Ser Glu Cys Lys Thr
95 100 105

Gly Ile Gly Asn Gly Tyr Arg Gly Thr Met Ser Arg Thr Lys Ser
110 115 120

Gly Val Ala Cys Gln Lys Trp Gly Ala Thr Phe Pro His Val Pro
125 130 135

Asn Tyr Ser Pro Ser Thr His Pro Asn Glu Gly Leu Glu Glu Asn
140 145 150

Tyr Cys Arg Asn Pro Asp Asn Asp Glu Gln Gly Pro Trp Cys Tyr
155 160 165

Thr Thr Asp Pro Asp Lys Arg Tyr Asp Tyr Cys Asn Ile Pro Glu
170 175 180

Cys Glu Glu Glu Cys Met Tyr Cys Ser Gly Glu Lys Tyr Glu Gly
185 190 195

Lys Ile Ser Lys Thr Met Ser Gly Leu Asp Cys Gln Ala Trp Asp
200 205 210

Ser Gln Ser Pro His Ala His Gly Tyr Ile Pro Ala Lys Phe Pro
215 220 225

Ser Lys Asn Leu Lys Met Asn Tyr Cys His Asn Pro Asp Gly Glu
230 235 240

Pro Arg Pro Trp Cys Phe Thr Thr Asp Pro Thr Lys Arg Trp Glu
245 250 255

Tyr Cys Asp Ile Pro Arg Cys Thr Thr Pro Pro Pro Pro Pro Ser
260 265 270

Pro Thr Tyr Gln Cys Leu Lys Gly Arg Gly Glu Asn Tyr Arg Gly
275 280 285

Thr Val Ser Val Thr Val Ser Gly Lys Thr Cys Gln Arg Trp Ser
290 295 300

Glu Gln Thr Pro His Arg His Asn Arg Thr Pro Glu Asn Phe Pro
305 310 315

-continued

| | | | | | | | | | | | | | | |
|---|---|---|---|---|---|---|---|---|---|---|---|---|---|---|
| Cys | Lys | Asn | Leu | Glu | Glu | Asn | Tyr | Cys | Arg | Asn | Pro | Asp | Gly | Glu |
| | | | | 320 | | | | | 325 | | | | | 330 |
| Thr | Ala | Pro | Trp | Cys | Tyr | Thr | Thr | Asp | Ser | Gln | Leu | Arg | Trp | Glu |
| | | | | 335 | | | | | 340 | | | | | 345 |
| Tyr | Cys | Glu | Ile | Pro | Ser | Cys | Glu | Ser | Ser | Ala | Ser | Pro | Asp | Gln |
| | | | | 350 | | | | | 355 | | | | | 360 |
| Ser | Asp | Ser | Ser | Val | Pro | Pro | Glu | Glu | Gln | Thr | Pro | Val | Val | Gln |
| | | | | 365 | | | | | 370 | | | | | 375 |
| Glu | Cys | Tyr | Gln | Ser | Asp | Gly | Gln | Ser | Tyr | Arg | Gly | Thr | Ser | Ser |
| | | | | 380 | | | | | 385 | | | | | 390 |
| Thr | Thr | Ile | Thr | Gly | Lys | Lys | Cys | Gln | Ser | Trp | Ala | Ala | Met | Phe |
| | | | | 395 | | | | | 400 | | | | | 405 |
| Pro | His | Arg | His | Ser | Lys | Thr | Pro | Glu | Asn | Phe | Pro | Asp | Ala | Gly |
| | | | | 410 | | | | | 415 | | | | | 420 |
| Leu | Glu | Met | Asn | Tyr | Cys | Arg | Asn | Pro | Asp | Gly | Asp | Lys | Gly | Pro |
| | | | | 425 | | | | | 430 | | | | | 435 |
| Trp | Cys | Tyr | Thr | Thr | Asp | Pro | Ser | Val | Arg | Trp | Glu | Tyr | Cys | Asn |
| | | | | 440 | | | | | 445 | | | | | 450 |
| Leu | Lys | Arg | Cys | Ser | Glu | Thr | Gly | Gly | Ser | Val | Val | Glu | Leu | Pro |
| | | | | 455 | | | | | 460 | | | | | 465 |
| Thr | Val | Ser | Gln | Glu | Pro | Ser | Gly | Pro | Ser | Asp | Ser | Glu | Thr | Asp |
| | | | | 470 | | | | | 475 | | | | | 480 |
| Cys | Met | Tyr | Gly | Asn | Gly | Lys | Asp | Tyr | Arg | Gly | Lys | Thr | Ala | Val |
| | | | | 485 | | | | | 490 | | | | | 495 |
| Thr | Ala | Ala | Gly | Thr | Pro | Cys | Gln | Gly | Trp | Ala | Ala | Gln | Glu | Pro |
| | | | | 500 | | | | | 505 | | | | | 510 |
| His | Arg | His | Ser | Ile | Phe | Thr | Pro | Gln | Thr | Asn | Pro | Arg | Ala | Asp |
| | | | | 515 | | | | | 520 | | | | | 525 |
| Leu | Glu | Lys | Asn | Tyr | Cys | Arg | Asn | Pro | Asp | Gly | Asp | Val | Asn | Gly |
| | | | | 530 | | | | | 535 | | | | | 540 |
| Pro | Trp | Cys | Tyr | Thr | Thr | Asn | Pro | Arg | Lys | Leu | Tyr | Asp | Tyr | Cys |
| | | | | 545 | | | | | 550 | | | | | 555 |
| Asp | Ile | Pro | Leu | Cys | Ala | Ser | Ala | Ser | Ser | Phe | Glu | Cys | Gly | Lys |
| | | | | 560 | | | | | 565 | | | | | 570 |
| Pro | Gln | Val | Glu | Pro | Lys | Lys | Cys | Pro | Gly | Arg | Val | Val | Gly | Gly |
| | | | | 575 | | | | | 580 | | | | | 585 |
| Cys | Val | Ala | Asn | Pro | His | Ser | Trp | Pro | Trp | Gln | Ile | Ser | Leu | Arg |
| | | | | 590 | | | | | 595 | | | | | 600 |
| Thr | Arg | Phe | Thr | Gly | Gln | His | Phe | Cys | Gly | Gly | Thr | Leu | Ile | Ala |
| | | | | 605 | | | | | 610 | | | | | 615 |
| Pro | Glu | Trp | Val | Leu | Thr | Ala | Ala | His | Cys | Leu | Glu | Lys | Ser | Ser |
| | | | | 620 | | | | | 625 | | | | | 630 |
| Arg | Pro | Glu | Phe | Tyr | Lys | Val | Ile | Leu | Gly | Ala | His | Glu | Glu | Tyr |
| | | | | 635 | | | | | 640 | | | | | 645 |
| Ile | Arg | Gly | Leu | Asp | Val | Gln | Glu | Ile | Ser | Val | Ala | Lys | Leu | Ile |
| | | | | 650 | | | | | 655 | | | | | 660 |
| Leu | Glu | Pro | Asn | Asn | Arg | Asp | Ile | Ala | Leu | Leu | Lys | Leu | Ser | Arg |
| | | | | 665 | | | | | 670 | | | | | 675 |
| Pro | Ala | Thr | Ile | Thr | Asp | Lys | Val | Ile | Pro | Ala | Cys | Leu | Pro | Ser |
| | | | | 680 | | | | | 685 | | | | | 690 |
| Pro | Asn | Tyr | Met | Val | Ala | Asp | Arg | Thr | Ile | Cys | Tyr | Ile | Thr | Gly |
| | | | | 695 | | | | | 700 | | | | | 705 |
| Trp | Gly | Glu | Thr | Gln | Gly | Thr | Phe | Gly | Ala | Gly | Arg | Leu | Lys | Glu |
| | | | | 710 | | | | | 715 | | | | | 720 |

-continued

Ala Gln Leu Pro Val Ile Glu Asn Lys Val Cys Asn Arg Val Glu
725 730 735

Tyr Leu Asn Asn Arg Val Lys Ser Thr Glu Leu Cys Ala Gly Gln
740 745 750

Leu Ala Gly Gly Val Asp Ser Cys Gln Gly Asp Ser Gly Gly Pro
755 760 765

Leu Val Cys Phe Glu Lys Asp Lys Tyr Ile Leu Gln Gly Val Thr
770 775 780

Ser Trp Gly Leu Gly Cys Ala Arg Pro Asn Lys Pro Gly Val Tyr
785 790 795

Val Arg Val Ser Arg Phe Val Asp Trp Ile Glu Arg Glu Met Arg
800 805 810

Asn Asn
812

( 2 ) INFORMATION FOR SEQ ID NO: 2:

( i ) SEQUENCE CHARACTERISTICS:
( A ) LENGTH: 339
( B ) TYPE: amino acid
( D ) TOPOLOGY: linear ( x i ) SEQUENCE DESCRIPTION: SEQ ID NO: 2:

Val Tyr Leu Ser Glu Cys Lys Thr Gly Ile Gly Asn Gly Tyr Arg
1 5 10 15

Gly Thr Met Ser Arg Thr Lys Ser Gly Val Ala Cys Gln Lys Trp
20 25 30

Gly Ala Thr Phe Pro His Val Pro Asn Tyr Ser Pro Ser Thr His
35 40 45

Pro Asn Glu Gly Leu Glu Glu Asn Tyr Cys Arg Asn Pro Asp Asn
50 55 60

Asp Glu Gln Gly Pro Trp Cys Tyr Thr Thr Asp Pro Asp Lys Arg
65 70 75

Tyr Asp Tyr Cys Asn Ile Pro Glu Cys Glu Glu Glu Cys Met Tyr
80 85 90

Cys Ser Gly Glu Lys Tyr Glu Gly Lys Ile Ser Lys Thr Met Ser
95 100 105

Gly Leu Asp Cys Gln Ala Trp Asp Ser Gln Ser Pro His Ala His
110 115 120

Gly Tyr Ile Pro Ala Lys Phe Pro Ser Lys Asn Leu Lys Met Asn
125 130 135

Tyr Cys His Asn Pro Asp Gly Glu Pro Arg Pro Trp Cys Phe Thr
140 145 150

Thr Asp Pro Thr Lys Arg Trp Glu Tyr Cys Asp Ile Pro Arg Cys
155 160 165

Thr Thr Pro Pro Pro Pro Pro Ser Pro Thr Tyr Gln Cys Leu Lys
170 175 180

Gly Arg Gly Glu Asn Tyr Arg Gly Thr Val Ser Val Thr Val Ser
185 190 195

Gly Lys Thr Cys Gln Arg Trp Ser Glu Gln Thr Pro His Arg His
200 205 210

Asn Arg Thr Pro Glu Asn Phe Pro Cys Lys Asn Leu Glu Glu Asn
215 220 225

Tyr Cys Arg Asn Pro Asp Gly Glu Thr Ala Pro Trp Cys Tyr Thr
230 235 240

-continued

Thr Asp Ser Gln Leu Arg Trp Glu Tyr Cys Glu Ile Pro Ser Cys
245 250 255

Glu Ser Ser Ala Ser Pro Asp Gln Ser Asp Ser Ser Val Pro Pro
260 265 270

Glu Glu Gln Thr Pro Val Val Gln Glu Cys Tyr Gln Ser Asp Gly
275 280 285

Gln Ser Tyr Arg Gly Thr Ser Ser Thr Thr Ile Thr Gly Lys Lys
290 295 300

Cys Gln Ser Trp Ala Ala Met Phe Pro His Arg His Ser Lys Thr
305 310 315

Pro Glu Asn Phe Pro Asp Ala Gly Leu Glu Met Asn Tyr Cys Arg
320 325 330

Asn Pro Asp Gly Asp Lys Gly Pro Trp
335 339

( 2 ) INFORMATION FOR SEQ ID NO: 3:

( i ) SEQUENCE CHARACTERISTICS:
( A ) LENGTH: 339
( B ) TYPE: amino acid
( D ) TOPOLOGY: linear ( x i ) SEQUENCE DESCRIPTION: SEQ ID NO: 3:

Val Tyr Leu Ser Glu Cys Lys Thr Gly Asn Gly Lys Asn Tyr Arg
1 5 10 15

Gly Thr Met Ser Lys Thr Lys Asn Gly Ile Thr Cys Gln Lys Trp
20 25 30

Ser Ser Thr Ser Pro His Arg Pro Arg Phe Ser Pro Ala Thr His
35 40 45

Pro Ser Glu Gly Leu Glu Glu Asn Tyr Cys Arg Asn Pro Asp Asn
50 55 60

Asp Pro Gln Gly Pro Trp Cys Tyr Thr Thr Asp Pro Glu Lys Arg
65 70 75

Tyr Asp Tyr Cys Asp Ile Leu Glu Cys Glu Glu Glu Cys Met His
80 85 90

Cys Ser Gly Glu Asn Tyr Asp Gly Lys Ile Ser Lys Thr Met Ser
95 100 105

Gly Leu Glu Cys Gln Ala Trp Asp Ser Gln Ser Pro His Ala His
110 115 120

Gly Tyr Ile Pro Ser Lys Phe Pro Asn Lys Asn Leu Lys Lys Asn
125 130 135

Tyr Cys Arg Asn Pro Asp Arg Glu Leu Arg Pro Trp Cys Phe Thr
140 145 150

Thr Asp Pro Asn Lys Arg Trp Glu Leu Cys Asp Ile Pro Arg Cys
155 160 165

Thr Thr Pro Pro Pro Ser Ser Gly Pro Thr Tyr Gln Cys Leu Lys
170 175 180

Gly Thr Gly Glu Asn Tyr Arg Gly Asn Val Ala Val Thr Val Ser
185 190 195

Gly His Thr Cys Gln His Trp Ser Ala Gln Thr Pro His Thr His
200 205 210

Asn Arg Thr Pro Glu Asn Phe Pro Cys Lys Asn Leu Asp Glu Asn
215 220 225

Tyr Cys Arg Asn Pro Asp Gly Lys Arg Ala Pro Trp Cys His Thr
230 235 240

Thr Asn Ser Gln Val Arg Trp Glu Tyr Cys Lys Ile Pro Ser Cys

-continued 245 250 255

Asp Ser Ser Pro Val Ser Thr Glu Gln Leu Ala Pro Thr Ala Pro
260 265 270

Pro Glu Leu Thr Pro Val Val Gln Asp Cys Tyr His Gly Asp Gly
275 280 285

Gln Ser Tyr Arg Gly Thr Ser Ser Thr Thr Thr Thr Gly Lys Lys
290 295 300

Cys Gln Ser Trp Ser Ser Met Thr Pro His Arg His Gln Lys Thr
305 310 315

Pro Glu Asn Tyr Pro Asn Ala Gly Leu Thr Met Asn Tyr Cys Arg
320 325 330

Asn Pro Asp Ala Asp Lys Gly Pro Trp
335 339

( 2 ) INFORMATION FOR SEQ ID NO: 4:

( i ) SEQUENCE CHARACTERISTICS:
( A ) LENGTH: 339
( B ) TYPE: amino acid
( D ) TOPOLOGY: linear ( x i ) SEQUENCE DESCRIPTION: SEQ ID NO: 4:

Val Tyr Leu Ser Glu Cys Lys Thr Gly Asn Gly Lys Asn Tyr Arg
1 5 10 15

Gly Thr Met Ser Lys Thr Arg Thr Gly Ile Thr Cys Gln Lys Trp
20 25 30

Ser Ser Thr Ser Pro His Arg Pro Thr Phe Ser Pro Ala Thr His
35 40 45

Pro Ser Glu Gly Leu Glu Glu Asn Tyr Cys Arg Asn Pro Asp Asn
50 55 60

Asp Gly Gln Gly Pro Trp Cys Tyr Thr Thr Asp Pro Glu Glu Arg
65 70 75

Phe Asp Tyr Cys Asp Ile Pro Glu Cys Glu Asp Glu Cys Met His
80 85 90

Cys Ser Gly Glu Asn Tyr Asp Gly Lys Ile Ser Lys Thr Met Ser
95 100 105

Gly Leu Glu Cys Gln Ala Trp Asp Ser Gln Ser Pro His Ala His
110 115 120

Gly Tyr Ile Pro Ser Lys Phe Pro Asn Lys Asn Leu Lys Lys Asn
125 130 135

Tyr Cys Arg Asn Pro Asp Gly Glu Pro Arg Pro Trp Cys Phe Thr
140 145 150

Thr Asp Pro Asn Lys Arg Trp Glu Leu Cys Asp Ile Pro Arg Cys
155 160 165

Thr Thr Pro Pro Pro Ser Ser Gly Pro Thr Tyr Gln Cys Leu Lys
170 175 180

Gly Thr Gly Glu Asn Tyr Arg Gly Asp Val Ala Val Thr Val Ser
185 190 195

Gly His Thr Cys His Gly Trp Ser Ala Gln Thr Pro His Thr His
200 205 210

Asn Arg Thr Pro Glu Asn Phe Pro Cys Lys Asn Leu Asp Glu Asn
215 220 225

Tyr Cys Arg Asn Pro Asp Gly Glu Lys Ala Pro Trp Cys Tyr Thr
230 235 240

Thr Asn Ser Gln Val Arg Trp Glu Tyr Cys Lys Ile Pro Ser Cys
245 250 255

-continued

| | | | | | | | | | | | | | | |
|---|---|---|---|---|---|---|---|---|---|---|---|---|---|---|
| Glu | Ser | Ser | Pro | Val<br>260 | Ser | Thr | Glu | Pro | Leu<br>265 | Asp | Pro | Thr | Ala | Pro<br>270 |
| Pro | Glu | Leu | Thr | Pro<br>275 | Val | Val | Gln | Glu | Cys<br>280 | Tyr | His | Gly | Asp | Gly<br>285 |
| Gln | Ser | Tyr | Arg | Gly<br>290 | Thr | Ser | Ser | Thr | Thr<br>295 | Thr | Thr | Gly | Lys | Lys<br>300 |
| Cys | Gln | Ser | Trp | Ser<br>305 | Ser | Met | Thr | Pro | His<br>310 | Trp | His | Glu | Lys | Thr<br>315 |
| Pro | Glu | Asn | Phe | Pro<br>320 | Asn | Ala | Gly | Leu | Thr<br>325 | Met | Asn | Tyr | Cys | Arg<br>330 |
| Asn | Pro | Asp | Ala | Asp<br>335 | Lys | Gly | Pro | Trp<br>339 | | | | | | |

( 2 ) INFORMATION FOR SEQ ID NO: 5:

( i ) SEQUENCE CHARACTERISTICS:
( A ) LENGTH: 339
( B ) TYPE: amino acid
( D ) TOPOLOGY: linear ( x i ) SEQUENCE DESCRIPTION: SEQ ID NO: 5:

| | | | | | | | | | | | | | | |
|---|---|---|---|---|---|---|---|---|---|---|---|---|---|---|
| Ile<br>1 | Tyr | Leu | Ser | Glu<br>5 | Cys | Lys | Thr | Gly | Asn<br>10 | Gly | Lys | Asn | Tyr | Arg<br>15 |
| Gly | Thr | Thr | Ser | Lys<br>20 | Thr | Lys | Ser | Gly | Val<br>25 | Ile | Cys | Gln | Lys | Trp<br>30 |
| Ser | Val | Ser | Ser | Pro<br>35 | His | Ile | Pro | Lys | Tyr<br>40 | Ser | Pro | Glu | Lys | Phe<br>45 |
| Pro | Leu | Ala | Gly | Leu<br>50 | Glu | Glu | Asn | Tyr | Cys<br>55 | Arg | Asn | Pro | Asp | Asn<br>60 |
| Asp | Glu | Lys | Gly | Pro<br>65 | Trp | Cys | Tyr | Thr | Thr<br>70 | Asp | Pro | Glu | Thr | Arg<br>75 |
| Phe | Asp | Tyr | Cys | Asp<br>80 | Ile | Pro | Glu | Cys | Glu<br>85 | Asp | Glu | Cys | Met | His<br>90 |
| Cys | Ser | Gly | Glu | His<br>95 | Tyr | Glu | Gly | Lys | Ile<br>100 | Ser | Lys | Thr | Met | Ser<br>105 |
| Gly | Ile | Glu | Cys | Gln<br>110 | Ser | Trp | Gly | Ser | Gln<br>115 | Ser | Pro | His | Ala | His<br>120 |
| Gly | Tyr | Leu | Pro | Ser<br>125 | Lys | Phe | Pro | Asn | Lys<br>130 | Asn | Leu | Lys | Met | Asn<br>135 |
| Tyr | Cys | Arg | Asn | Pro<br>140 | Asp | Gly | Glu | Pro | Arg<br>145 | Pro | Trp | Cys | Phe | Thr<br>150 |
| Thr | Asp | Pro | Asn | Lys<br>155 | Arg | Trp | Glu | Phe | Cys<br>160 | Asp | Ile | Pro | Arg | Cys<br>165 |
| Thr | Thr | Pro | Pro | Pro<br>170 | Thr | Ser | Gly | Pro | Thr<br>175 | Tyr | Gln | Cys | Leu | Lys<br>180 |
| Gly | Arg | Gly | Glu | Asn<br>185 | Tyr | Arg | Gly | Thr | Val<br>190 | Ser | Val | Thr | Ala | Ser<br>195 |
| Gly | His | Thr | Cys | Gln<br>200 | Arg | Trp | Ser | Ala | Gln<br>205 | Ser | Pro | His | Lys | His<br>210 |
| Asn | Arg | Thr | Pro | Glu<br>215 | Asn | Phe | Pro | Cys | Lys<br>220 | Asn | Leu | Glu | Glu | Asn<br>225 |
| Tyr | Cys | Arg | Asn | Pro<br>230 | Asp | Gly | Glu | Thr | Ala<br>235 | Pro | Trp | Cys | Tyr | Thr<br>240 |
| Thr | Asp | Ser | Glu | Val<br>245 | Arg | Trp | Asp | Tyr | Cys<br>250 | Lys | Ile | Pro | Ser | Cys<br>255 |

-continued

Gly Ser Ser Thr Thr Ser Thr Glu His Leu Asp Ala Pro Val Pro
260 265 270

Pro Glu Gln Thr Pro Val Ala Gln Asp Cys Tyr Arg Gly Asn Gly
275 280 285

Glu Ser Tyr Arg Gly Thr Ser Ser Thr Thr Ile Thr Gly Arg Lys
290 295 300

Cys Gln Ser Trp Val Ser Met Thr Pro His Arg His Glu Lys Thr
305 310 315

Pro Gly Asn Phe Pro Asn Ala Gly Leu Thr Met Asn Tyr Cys Arg
320 325 330

Asn Pro Asp Ala Asp Lys Ser Pro Trp
335 339

( 2 ) INFORMATION FOR SEQ ID NO: 6:

( i ) SEQUENCE CHARACTERISTICS:

( A ) LENGTH: 339

( B ) TYPE: amino acid ( D ) TOPOLOGY: linear ( x i ) SEQUENCE DESCRIPTION: SEQ ID NO: 6:

Ile Tyr Leu Leu Glu Cys Lys Thr Gly Asn Gly Gln Thr Tyr Arg
1 5 10 15

Gly Thr Thr Ala Glu Thr Lys Ser Gly Val Thr Cys Gln Lys Trp
20 25 30

Ser Ala Thr Ser Pro His Val Pro Lys Phe Ser Pro Glu Lys Phe
35 40 45

Pro Leu Ala Gly Leu Glu Glu Asn Tyr Cys Arg Asn Pro Asp Asn
50 55 60

Asp Glu Asn Gly Pro Trp Cys Tyr Thr Thr Asp Pro Asp Lys Arg
65 70 75

Tyr Asp Tyr Cys Asp Ile Pro Glu Cys Glu Asp Lys Cys Met His
80 85 90

Cys Ser Gly Glu Asn Tyr Glu Gly Lys Ile Ala Lys Thr Met Ser
95 100 105

Gly Arg Asp Cys Gln Ala Trp Asp Ser Gln Ser Pro His Ala His
110 115 120

Gly Tyr Ile Pro Ser Lys Phe Pro Asn Lys Asn Leu Lys Met Asn
125 130 135

Tyr Cys Arg Asn Pro Asp Gly Glu Pro Arg Pro Trp Cys Phe Thr
140 145 150

Thr Asp Pro Gln Lys Arg Trp Glu Phe Cys Asp Ile Pro Arg Cys
155 160 165

Thr Thr Pro Pro Pro Ser Ser Gly Pro Lys Tyr Gln Cys Leu Lys
170 175 180

Gly Thr Gly Lys Asn Tyr Gly Gly Thr Val Ala Val Thr Glu Ser
185 190 195

Gly His Thr Cys Gln Arg Trp Ser Glu Gln Thr Pro His Lys His
200 205 210

Asn Arg Thr Pro Glu Asn Phe Pro Cys Lys Asn Leu Glu Glu Asn
215 220 225

Tyr Cys Arg Asn Pro Asp Gly Glu Lys Ala Pro Trp Cys Tyr Thr
230 235 240

Thr Asn Ser Glu Val Arg Trp Glu Tyr Cys Thr Ile Pro Ser Cys
245 250 255

Glu Ser Ser Pro Leu Ser Thr Glu Arg Met Asp Val Pro Val Pro

-continued

| | | | | | | | | | | | | | | |
|---|---|---|---|---|---|---|---|---|---|---|---|---|---|---|
| | | | | 260 | | | | | 265 | | | | | 270 |
| Pro | Glu | Gln | Thr | Pro | Val | Pro | Gln | Asp | Cys | Tyr | His | Gly | Asn | Gly |
| | | | | 275 | | | | | 280 | | | | | 285 |
| Gln | Ser | Tyr | Arg | Gly | Thr | Ser | Ser | Thr | Thr | Ile | Thr | Gly | Arg | Lys |
| | | | | 290 | | | | | 295 | | | | | 300 |
| Cys | Gln | Ser | Trp | Ser | Ser | Met | Thr | Pro | His | Arg | His | Leu | Lys | Thr |
| | | | | 305 | | | | | 310 | | | | | 315 |
| Pro | Glu | Asn | Tyr | Pro | Asn | Ala | Gly | Leu | Thr | Met | Asn | Tyr | Cys | Arg |
| | | | | 320 | | | | | 325 | | | | | 330 |
| Asn | Pro | Asp | Ala | Asp | Lys | Ser | Pro | Trp | | | | | | |
| | | | | 335 | | | | 339 | | | | | | |

NUCLEOTIDES ENCODING ANGIOSTATIN PROTEIN AND METHOD OF USE

This application is a CIP of application Ser. No. 07/248,629 filed Apr. 26, 1994, now U.S. Pat. No. 5,639,725.

FIELD OF THE INVENTION

The present invention relates to endothelial inhibitors, called angiostatin, which reversibly inhibit proliferation of endothelial cells. More particularly, the present invention relates to angiostatin proteins that can be isolated from body fluids such as blood or urine or can be synthesized by recombinant, enzymatic or chemical methods. The angiostatin is capable of inhibiting angiogenesis related diseases and modulating angiogenic processes. In addition, the present invention relates to diagnostic assays and kits for angiostatin measurement, to histochemical kits for localization of angiostatin, to molecular probes to monitor angiostatin biosynthesis, to antibodies that are specific for the angiostatin, to the development of peptide agonists and antagonists to the angiostatin receptor, to anti-angiostatin receptor-specific antibody agonists and antagonists, and to cytotoxic agents linked to angiostatin peptides.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The hypothesis that tumor growth is angiogenesis-dependent was first proposed in 1971. (Folkmnan J., Tumor angiogenesis: Therapeutic implications., *N. Engl. Jour. Med.* 285:1182 1186, 1971) In its simplest terms it states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire G H, et al. Vascular reactions of normal and malignant tumors in vivo. I. Vascular reactions of mice to wounds and to normal and neoplastic transplants. *J. Natl. Cancer Inst.* 6:73–85, 1945)

(2) Tumors grown in isolated perfused organs where blood vessels do not proliferate are limited to 1–2 $mm^3$ but expand rapidly to >1000 times this volume when they are transplanted to mice and become neovascularized. (Folkman J, et al., Tumor behavior in isolated perfused organs: In vitro growth and metastasis of biopsy material in rabbit thyroid and canine intestinal segments. *Annals of Surgery* 164:491–502, 1966)

(3) Tumor growth in the avascular cornea proceeds slowly and at a linear rate, but switches to exponential growth after neovascularization. (Gimbrone, M. A., Jr. et al., Tumor growth and neovascularization: An experimental model using the rabbit cornea. *J. Natl. Cancer Institute* 52:41–427, 1974)

(4) Tumors suspended in the aqueous fluid of the anterior chamber of the rabbit eye, remain viable, avascular and limited in size to <1 $mm^3$. Once they are implanted on the iris vascular bed, they become neovascularized and grow rapidly, reaching 16,000 times their original volume within 2 weeks. (Gimbrone M A Jr., et al., Tumor dormancy in vivo by prevention of neovascularization. *J. Exp. Med.* 136:261–276)

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton D., Avascular and vascular phases of tumor growth in the chick embryo. *British J. Cancer*, 35:347–356, 1977)

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien W., et al., The blood supply of experimental liver metastases. II. A microcirculatory study of normal and tumor vessels of the liver with the use of perfused silicone rubber. *Surgery* 68:334–340, 1970)

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman J, et al., Induction of angiogenesis during the transition from hyperplasia to neoplasia. *Nature* 339:58–61, 1989)

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim K J, et al., Inhibition of vascular endothelial growth factor-induced angiogenesis suppresses tumor growth in vivo. *Nature* 362:841–844, 1993)

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori A, et al., Suppression of solid tumor growth by immunoneutralizing monoclonal antibody against human basic fibroblast growth factor. *Cancer Research*, 51:6180–6184, 1991)

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross J L, et al. Modulation of solid tumor growth in vivo by bFGF. *Proc. Amer. Assoc. Canc. Res.* 31:79, 1990)

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber D, et al., Angioinhibins: Synthetic analogues of fumagillin which inhibit angiogenesis and suppress tumor growth. *Nature*, 48:555–557, 1990) There is also indirect clinical evidence that tumor growth is angiogenesis dependent.

(12) Human retinoblastomas that are metastatic to the vitreous develop into avascular spheroids which are restricted to less than 1 $mm^3$ despite the fact that they are viable and incorporate $^3H$-thymidine (when removed from an enucleated eye and analyzed in vitro).

(13) Carcinoma of the ovary metastasizes to the peritoneal membrane as tiny avascular white seeds (1–3 $mm^3$). These implants rarely grow larger until one or more of them becomes neovascularized.

(14) Intensity of neovascularization in breast cancer (Weidner N, et al., Tumor angiogenesis correlates with metastasis in invasive breast carcinoma. *N. Engl. J. Med.* 324:1–8, 1991, and Weidner N, et al., Tumor angiogenesis: A new significant and independent prognostic indicator in early-stage breast carcinoma, *J Natl. Cancer Inst.* 84:1875–1887, 1992) and in prostate cancer (Weidner N, Carroll P R, Flax J, Blumenfeld W, Folkman J. Tumor angiogenesis correlates with metastasis in invasive prostate carcinoma. *American Journal of Pathology*, 143(2):401–409, 1993) correlates highly with risk of future metastasis.

(15) Metastasis from human cutaneous melanoma is rare prior to neovascularization. The onset of neovascularization leads to increased thickness of the lesion and an increasing risk of metastasis. (Srivastava A, et al., The prognostic significance of tumor vascularity in intermediate thickness (0.76–4.0 mm thick) skin melanoma. *Amer. J. Pathol.* 133:419–423, 1988)

(16) In bladder cancer, the urinary level of an angiogenic peptide, bFGF, is a more sensitive indicator of status and extent of disease than is cytology. (Nguyen M, et al., Elevated levels of an angiogenic peptide, basic fibroblast growth factor, in urine of bladder cancer patients. *J. Natl. Cancer Inst.* 85:241–242, 1993)

Thus, it is clear that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

What is needed therefore is a composition and method which can inhibit the unwanted growth of blood vessels, especially into tumors. Also needed is a method for detecting, measuring, and localizing the composition. The composition should be able to overcome the activity of endogenous growth factors in premetastatic tumors and prevent the formation of the capillaries in the tumors thereby inhibiting the growth of the tumors. The composition, fragments of the composition, and antibodies specific to the composition, should also be able to modulate the formation of capillaries in other angiogenic processes, such as wound healing and reproduction. The composition and method for inhibiting angiogenesis should preferably be non-toxic and produce few side effects. Also needed is a method for detecting, measuring, and localizing the binding sites for the composition as well as sites of biosynthesis of the composition. The composition and fragments of the composition should be capable of being conjugated to other molecules for both radioactive and non-radioactive labeling purposes

SUMMARY OF THE INVENTION

In accordance with the present invention, compositions and methods are provided that are effective in inhibiting unwanted angiogenesis, especially angiogenesis related to tumor growth. The present invention includes a protein, which has been named "angiostatin", defined by its ability to overcome the angiogenic activity of endogenous growth factors such as bFGF, in vitro. Angiostatin comprises a protein having a molecular weight of between approximately 38 kilodaltons and 45 kilodaltons as determined by reducing polyacrylamide gel electrophoresis and having an amino acid sequence substantially similar to that of a fragment of murine plasminogen beginning at amino acid number 98 of an intact murine plasminogen molecule (SEQ ID NO:2).

The amino acid sequence of angiostatin varies slightly between species. For example, in human angiostatin the amino acid sequence is substantially similar to the sequence of the above described murine plasminogen fragment, although an active human angiostatin sequence may start at either amino acid number 97 or 99 of an intact human plasminogen amino acid sequence. Further, human plasminogen has similar antiangiogenic activity as shown in a mouse tumor model. It is to be understood that the number of amino acids in the active angiostatin molecule may vary and all amino acid sequences that have endothelial inhibiting activity are contemplated as being included in the present invention.

The present invention provides methods and compositions for treating diseases and processes mediated by undesired and uncontrolled angiogenesis by administering to a human or animal a composition comprising a substantially purified angiostatin or angiostatin derivative in a dosage sufficient to inhibit angiogenesis. The present invention is particularly useful for treating or for repressing the growth of tumors. Administration of angiostatin to a human or animal with prevascularized metastasized tumors will prevent the growth or expansion of those tumors.

The present invention also includes diagnostic methods and kits for detection and measurement of angiostatin in biological fluids and tissues, and for localization of angiostatin in tissues. The diagnostic method and kit can be in any configuration well known to those of ordinary skill in the art. The present invention also includes antibodies specific for the angiostatin and antibodies that inhibit the binding of antibodies specific for the angiostatin. These antibodies can be polyclonal antibodies or monoclonal antibodies. The antibodies specific for the angiostatin can be used in diagnostic kits to detect the presence and quantity of angiostatin which is diagnostic or prognostic for the occurrence or recurrence of cancer or other disease mediated by angiogenesis. Antibodies specific for angiostatin may also be administered to a human or animal to passively immunize the human or animal against angiostatin, thereby reducing angiogenic inhibition.

The present invention also includes diagnostic methods and kits for detecting the presence and quantity of antibodies that bind angiostatin in body fluids. The diagnostic method and kit can be in any configuration well known to those of ordinary skill in the art.

The present invention also includes anti-angiostatin receptor-specific antibodies that bind to the receptor and transmit the appropriate signal to the cell and act as agonists or antagonists.

The present invention also includes angiostatin peptide fragments that can be labeled isotopically or with other molecules or proteins for use in the detection and visualization of angiostastin binding sites with state of the art techniques, including, but not limited to, positron emission tomography, autoradiography, flow cytometry, radioreceptor binding assays, and immunohistochemistry.

These angiostatin peptides also act as agonists and antagonists at the angiostatin receptor, thereby enhancing or blocking the biological activity of angiostatin. Such peptides are used in the isolation of the angiostatin receptor.

The present invention also includes angiostatin, angiostatin fragments, angiostatin antisera, or angiostatin receptor agonists and antagonists linked to cytotoxic agents for therapeutic and research applications.

The present invention includes molecular probes for the ribonucleic acid and deoxyribonucleic acid involved in transcription and translation of angiostatin. These molecular probes provide means to detect and measure angiostatin biosynthesis in tissues and cells.

Accordingly, it is an object of the present invention to provide a composition comprising an angiostatin.

It is another object of the present invention to provide a method of treating diseases and processes that are mediated by angiogenesis.

It is yet another object of the present invention to provide a diagnostic or prognostic method and kit for detecting the presence and amount of angiostatin in a body fluid or tissue.

It is yet another object of the present invention to provide a method and composition for treating diseases and processes that are mediated by angiogenesis including, but not limited to, hemangioma, solid tumors, leukemia, metastasis, telangiectasia psoriasis scleroderma, pyogenic granuloma, myocardial angiogenesis, plaque neovascularization, corornay collaterals, cerebral collaterals, arteriovenous malformations, ischeniic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Heliobacter related diseases, fractures, keloids, vasculogenesis, hematopoiesis, ovulation, menstruation, placentation, and cat scratch fever.

It is another object of the present invention to provide a composition for treating or repressing the growth of a cancer.

It is an object of the present invention to provide compounds that modulate or mimic the production or activity of enzymes that produce angiostatin in vivo or in vitro.

It is a further object of the present invention to provide angiostatin or anti-angiostatin antibodies by direct injection of angiostatin DNA into a human or animal needing such angiostatin or anti-angiostatin antibodies.

It is an object of present invention to provide a method for detecting and quantifying the presence of an antibody specific for an angiostatin in a body fluid.

Still another object of the present invention is to provide a composition consisting of antibodies to angiostatin that are selective for specific regions of the angiostatin molecule that do not recognize plasminogen.

It is another object of the present invention to provide a method for the detection or prognosis of cancer.

It is another object of the present invention to provide a composition for use in visualizing and quantitating sites of angiostatin binding in vivo and in vitro.

It is yet another object of the present invention to provide a composition for use in detection and quantification of angiostatin biosynthesis.

It is yet another object of the present invention to provide a therapy for cancer that has minimal side effects.

Still another object of the present invention is to provide a composition comprising angiostatin or an angiostatin peptide linked to a cytotoxic agent for treating or repressing the growth of a cancer.

Another object of the present invention is to provide a method for targeted delivery of angiostatin-related compositions to specific locations. These and other objects, features and advantages of the present invention will become apparent after a review of the following detailed description of the disclosed embodiments and the appended claims.

BRIEF DESCRIPTION OF THE FIGURES

FIG. 1 shows SEQ ID NO:1, the amino acid sequence of the whole murine plasminogen.

FIG. 2 shows the beginning sequence of the angiostatin for murine (SEQ ID NO:2) and compares the murine sequence with corresponding human (SEQ ID NO:3), Rhesus monkey (SEQ ID NO:4), porcine (SEQ ID NO:5) and bovine (SEQ ID NO:6) plasminogen peptide fragments. The mouse sequence is listed first, followed by human, Rhesus, porcine and bovine.

FIG. 3 shows BrdU labeling index of tumor cells in the lung in the presence or absence of a primary tumor.

FIG. 4 shows Matrigel analysis of the influence of a Lewis lung primary tumor on bFGF driven angiogenesis in vivo.

FIG. 5 shows dose response curve for serum derived from mice bearing Lewis lung carcinoma (LLC-Low) versus serum from normal mice. Bovine capillary endothelial cells were assayed in a bFGF-driven 72-hour proliferation assay.

FIG. 6 shows that both low and high metastatic tumors contain endothelial mitogenic activity in their ascites, but only the low metastatic tumor line has endothelial inhibitory activity in the serum.

FIG. 7 shows a C4 Reverse Phase Chromatographic profile of partially purified serum or urine from tumor-bearing animals.

DETAILED DESCRIPTION

Figure 8:
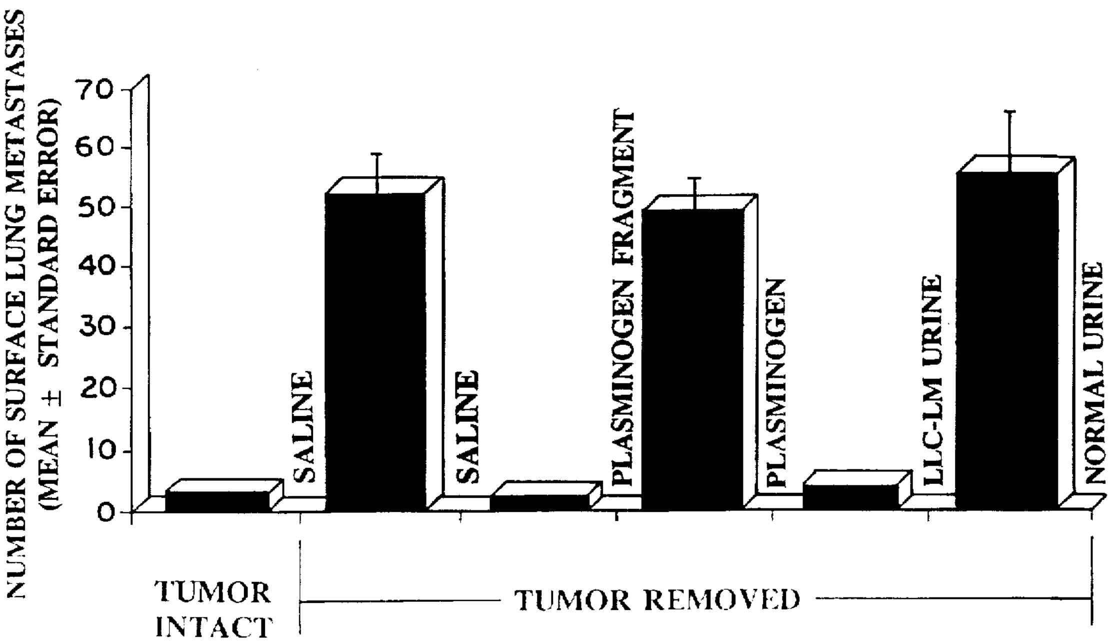
FIG. 8 shows surface lung metastases after the 13 day treatment of mice with intact plasminogen molecule, active fraction from a lysine binding site I preparation of human plasminogen, concentrated urine from tumor bearing mice and concentrated urine from normal mice.

The present invention includes compositions and methods for the detection and treatment of diseases and processes that are mediated by or associated with angiogenesis. The composition is angiostatin, which can be isolated from body fluids including, but not limited to, serum, urine and ascites, or synthesized by chemical or biological methods (e.g. cell culture, recombinant gene expression, peptide synthesis, and in vitro enzymatic catalysis of plasminogen or plasmin to yield active angiostatin). Recombinant techniques include gene amplification from DNA sources using the polymerase chain reaction (PCR), and gene amplification from RNA sources using reverse transcriptase/PCR. Angiostatin inhibits the growth of blood vessels into tissues such as unvascularized or vascularized tumors. The present invention includes a protein that has a molecular weight of approximately 38 to 45 kilodaltons (kD) that is capable of overcoming the angiogenic activity of endogenous growth factors such as bFGF, in vitro. Angiostatin is a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The term "substantially similar," when used in reference to angiostatin amino acid sequences, means an amino acid sequence having anti-angiogenic activity and having a molecular weight of approximately 38 kD to 45 kD, which also has a high degree of sequence homology to the peptide fragment of mouse plasminogen beginning approximately at amino acid number 98 in mouse plasminogen and weighing 38 kD to 45 kD. A high degree of homology means at least approximately 60% amino acid homology, desirably at least approximately 70% amino acid homology, and more desirably at least approximately 80% amino acid homology. The term "endothelial inhibiting activity" as used herein means the capability of a molecule to inhibit angiogenesis in general and, for example, to inhibit the growth of bovine capillary endothelial cells in culture in the presence of fibroblast growth factor.

The amino acid sequence of the complete murine plasminogen molecule is shown in FIG. 1 and in SEQ ID NO:1. The sequence for angiostatin begins approximately at amino acid 98. Active human angiostatin may start at either amino acid 97 or 99 of the intact human plasminogen molecule. The amino acid sequence of the first 339 amino acids of angiostatin from mouse is shown in FIG. 2, (SEQ ID NO:2), and is compared with the sequences of corresponding plasminogen peptide fragments from human (SEQ ID NO:3, Rhesus monkey (SEQ ID NO:4), porcine (SEQ ID NO:5) and bovine (SEQ ID NO:6) plasminogen. Given that these sequences are identical in well over 50% of their amino acids, it is to be understood that the amino acid sequence of the angiostatin is substantially similar among species. The total number of amino acids in angiostatin is not known precisely but is defined by the molecular weight of the active molecule. The amino acid sequence of the angiostatin of the present invention may vary depending upon from which species the plasminogen molecule is derived. Thus, although the angiostatin of the present invention that is derived from human plasminogen has a slightly different sequence than angiostatin derived from mouse it has anti-angiogenic activity as shown in a mouse tumor model.

Angiostatin has been shown to be capable of inhibiting the growth of endothelial cells in vitro. Angiostatin does not inhibit the growth of cell lines derived from other cell types. Specifically, angiostatin has no effect on Lewis lung carcinoma cell lines, mink lung epithelium, 3T3 fibroblasts, bovine aortic smooth muscle cells, bovine retinal pigment epithelium, MDCk cells (canine renal epithelium), WI38 cells (human fetal lung fibroblasts) EFN cells (murine fetal fibroblasts) and LM cells (murine connective tissue).

Angiostatin has a specific three dimensional conformation that is defined by the kringle region of the plasminogen molecule. (Robbins, K. C., "The plasminogen-plasmin enzyme system" *Hemostasis and Thrombosis, Basic Principles and Practice*, 2nd Edition, ed. by Colman, R. W. et al. J. B. Lippincott Company, pp. 340–357, 1987) There are five such kringle regions, which are conformationally related motifs and have substantial sequence homology, in the $NH_2$ terminal portion of the plasminogen molecule. The three dimensional conformation of angiostatin is believed to encompass plasminogen kringles 1 through 3 and a part of kringle 4. Each kringle region of the plasminogen molecule contains approximately 80 amino acids and contains 3 disulfide bonds. This cysteine motif is known to exist in other biologically active proteins. These proteins include, but are not limited to, prothrombin, hepatocyte growth factor, scatter factor and macrophage stimulating protein. (Yoshimura, T. et al., "Cloning, sequencing, and expression of human macrophage stimulating protein (MSP, MST1) confirms MSP as a member of the family of kringle proteins and locates the MSP gene on Chromosome 3" *J. Biol. Chem.*, Vol. 268, No. 21, pp. 15461–15468, 1993). It is contemplated that any isolated protein or peptide having a three dimensional kringle-like conformation or cysteine motif that has anti-angiogenic activity in vivo, is part of the present invention.

The present invention also includes the detection of the angiostatin in body fluids and tissues for the purpose of diagnosis or prognosis of diseases such as cancer. The present invention also includes the detection of angiostatin binding sites and receptors in cells and tissues. The present invention also includes methods of treating or preventing angiogenic diseases and processes including, but not limited to, arthritis and tumors by stimulating the production of angiostatin, and/or by administering substantially purified angiostatin, or angiostatin agonists or antagonists, and/or angiostatin antisera or antisera directed against angiostatin antisera to a patient. Additional treatment methods include administration of angiostatin, angiostatin fragments, angiostatin antisera, or angiostatin receptor agonists and antagonists linked to cytotoxic agents. It is to be understood that the angiostatin can be animal or human in origin. Angiostatin can also be produced synthetically by chemical reaction or by recombinant techniques in conjunction with expression systems. Angiostatin can also be produced by enzymatically cleaving isolated plasminogen or plasmin to generate peptides having anti-angiogenic activity. Angiostatin may also be produced by compounds that mimic the action of endogenous enzymes that cleave plasminogen to angiostatin. Angiostatin production may also be modulated by compounds that affect the activity of plasminogen cleaving enxymes.

Passive antibody therapy using antibodies that specifically bind angiostatin can be employed to modulate angiogenic-dependent processes such as reproduction, development, and wound healing and tissue repair. In addition, antisera directed to the Fab regions of angiostatin antibodies can be administered to block the ability of endogenous angiostatin antisera to bind angiostatin.

The present invention also encompasses gene therapy whereby the gene encoding angiostatin is regulated in vivo. For example, the gene regulation may be accomplished by administering compounds that bind to the angiostatin gene, or control regions associated with the angiostatin gene, or its corresponding RNA transcript to modify the rate of transcription or translation.

Angiostatin can be isolated on an HPLC C4 column (see Table 3). The angiostatin protein is eluted at 30 to 35% in an acetonitrile gradient. On a sodium dodecyl sulfate polyacrylamide gel electrophoresis (PAGE) gel under reducing conditions, the protein band with activity eluted as a single peak at approximately 38 kilodaltons.

The inventors have shown that a growing primary tumor is associated with the release into the blood stream of specific inhibitor(s) of endothelial cell proliferation, including angiostatin which can suppress angiogenesis within a metastasis and thereby inhibit the growth of the metastasis itself. The source of the angiostatin associated with the primary tumor is not known. The compound may be produced by degradation of plasminogen by a specific protease, or angiostatin could be produced by expression of a specific gene coding for angiostatin. The angiogenic phenotype of a primary tumor depends on production of angiogenic peptides in excess of endothelial cell inhibitors which are elaborated by normal cells, but are believed to be down-regulated during transformation to neoplasia. While production of angiostatin may be down-regulated in an individual tumor cell relative to production by its parent, the total inhibitor elaborated by the whole tumor may be sufficient to enter the circulation and suppress endothelial growth at remote sites of micrometastases. Angiostatin remains in the circulation for a significantly longer time than the angiogenic peptide(s) released by a primary tumor. Thus, the angiogenic peptides appear to act locally, whereas angiostatin acts globally and circulates in the blood with a relatively long half-life. The half-life of the angiostatin is approximately 12 hours to 5 days.

Although not wanting to be bound by the following hypothesis, it is believed that when a tumor becomes angiogenic it releases one or more angiogenic peptides (e.g., aFGF, bFGF, VEGF, IL-8, GM-CSF, etc.), which act locally, target endothelium in the neighborhood of a primary tumor from an extravascular direction, and do not circulate (or circulate with a short half-life). These angiogenic peptides must be produced in an amount sufficient to overcome the action of endothelial cell inhibitor (inhibitors of angiogenesis) for a primary tumor to continue to expand its population. Once such a primary tumor is growing well, it continues to release endothelial cell inhibitors into the circulation. According to this hypothesis, these inhibitors act at a distance from the primary tumor, target capillary endothelium of a metastasis from an intravascular direction, and continue to circulate. Thus, just at the time when a remote metastasis might begin to initiate angiogenesis, the capillary endothelium in its neighborhood could be swamped by incoming angiostatin. Once a primary tumor has reached sufficient size to cause angiostatin to be released continuously into the circulation, it is difficult for a second tumor implant (or a micrometastasis) to initiate or increase its own angiogenesis. If a second tumor implant (e.g., into the subcutaneous space, or into the cornea, or intravenously to the lung) occurs at the same time, or shortly after the primary tumor is implanted, the primary tumor will not be able to suppress the secondary tumor (because angiogenesis in the secondary tumor will already be well underway). If two tumors are implanted simultaneously (e.g., in opposite flanks), the inhibitors may have an equivalent inhibiting effect on each other.

The angiostatin of the present invention can be:

(i) Administered to tumor-bearing humans or animals as anti-angiogenic therapy.

(ii) Monitored in human or animal serum, urine, or tissues as prognostic markers.

(iii) Used as the basis to analyze serum and urine of cancer patients for similar angiostatic molecules.

It is contemplated as part of the present invention that angiostatin can be isolated from a body fluid such as blood or urine of patients or the angiostatin can be produced by recombinant DNA methods or synthetic peptide chemical methods that are well known to those of ordinary skill in the art. Protein purification methods are well known in the art and a specific example of a method for purifying angiostatin, and assaying for inhibitor activity is provided in the examples below. Isolation of human endogenous angiostatin is accomplished using similar techniques.

One example of a method of producing angiostatin using recombinant DNA techniques entails the steps of (1) identifying and purifying angiostatin as discussed above, and as more fully described below, (2) determining the N-terminal amino acid sequence of the purified inhibitor, (3) synthetically generating 5' and 3' DNA oligonucleotide primers for the angiostatin sequence, (4) amplifying the angiostatin gene sequence using polymerase, (5) inserting the amplified sequence into an appropriate vector such as an expression vector, (6) inserting the gene containing vector into a microorganism or other expression system capable of expressing the inhibitor gene, and (7) isolating the recombinantly produced inhibitor. The above techniques are more fully described in laboratory manuals such as "Molecular Cloning: A Laboratory Manual" Second Edition by Sambrook et al., Cold Spring Harbor Press, 1989. The DNA sequence of human plasminogen has been published (Browne, M. J., et al., "Expression of recombinant human plasminogen and aglycoplasminogen in HeLa cells" Fibrinolysis Vol.5 (4), 257–260, 1991) and is incorporated herein by reference. One example of such a recombinant expression system is *Echerichia coli* strain XL-1B pTrcHisA/HAsH4 available upon permission from the American Type Culture Collection 12301 Parklawn Drive, Rockville, Md. 20852 under ATCC Designation No. 98231 deposited on Oct. 23, 1996.

The gene for angiostatin may also be isolated from cells or tissue (such as tumor cells) that express high levels of angiostatin by (1) isolating messenger RNA from the tissue, (2) using reverse transcriptase to generate the corresponding DNA sequence and then (3) using PCR with the appropriate primers to amplify the DNA sequence coding for the active angiostatin amino acid sequence.

Yet another method of producing angiostatin, or biologically active fragments thereof, is by peptide synthesis. Once a biologically active fragment of an angiostatin is found using the assay system described more fully below, it can be sequenced, for example by automated peptide sequencing methods. Alternatively, once the gene or DNA sequence which codes for angiostatin is isolated, for example by the methods described above, the DNA sequence can be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, the fragment can be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for agonistic and antagonistic activity in vitro and in vivo. Peptide fragments that possess high affinity binding to tissues can be used to isolate the angiostatin receptor on affinity columns. Isolation and purification of the angiostatin receptor is a fundamental step towards elucidating the mechanism of action of angiostatin. This facilitates development of drugs to modulate the activity of the angiostatin receptor, the final pathway to biological activity. Isolation of the receptor enables the construction of nucleotide probes to monitor the location and synthesis of the receptor, using in situ and solution hybridization technology.

Angiostatin is effective in treating diseases or processes that are mediated by, or involve, angiogenesis. The present invention includes the method of treating an angiogenesis mediated disease with an effective amount of angiostatin or angiostatin agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Angiostatin is useful in the treatment of disease of excessive or abnormal stimulation of endothelial cells. These diseases include, but are not limited to, intestinal adhesions, atherosclerosis, scleroderma, and hypertrophic scars, i.e., keloids. Angiostatin can be used as a birth control agent by preventing vascularization required for embryo implantation. Angiostatin is useful in the treatment of diseases that have angiogenesis as a pathologic consequence such as cat scratch disease (*Rochele minalia quintosa*) and ulcers (*Helobacter pylori*).

The synthetic peptide fragments of angiostatin have a variety of uses. The peptide that binds to the angiostatin receptor with high specificity and avidity is radiolabeled and employed for visualization and quantitation of binding sites using autoradiographic and membrane binding techniques. This application provides important diagnostic and research tools. Knowledge of the binding properties of the angiostatin receptor facilitates investigation of the transduction mechanisms linked to the receptor.

In addition, labeling these peptides with short lived isotopes enables visualization of receptor binding sites in vivo using positron emission tomography or other modern radiographic techniques in order to locate tumors with angiostatin binding sites.

Systematic substitution of amino acids within these synthesized peptides yields high affinity peptide agonists and antagonists to the angiostatin receptor that enhance or diminish angiostatin binding to its receptor. Such agonists are used to suppress the growth of micrometastases, thereby limiting the spread of cancer. Antagonists to angiostatin are applied in situations of inadequate vascularization, to block the inhibitory effects of angiostatin and possibly promote angiogenesis. This treatment may have therapeutic effects to promote wound healing in diabetics.

Angiostatin peptides are employed to develop affinity columns for isolation of the angiostatin receptor from cultured tumor cells. Isolation and purification of the angiostatin receptor is followed by amino acid sequencing. Next, nucleotide probes are developed for insertion into vectors for expression of the receptor. These techniques are well known to those skilled in the art. Transfection of the angiostatin receptor into tumor cells enhances the responsiveness of these cells to endogenous or exogenous angiostatin and thereby decreasing the rate of metastatic growth.

Cytotoxic agents such as ricin, are linked to angiostatin, and high affinity angiostatin peptide fragments, thereby providing a tool for destruction of cells that bind angiostatin. These cells may be found in many locations, including but not limited to, micrometastases and primary tumors. Peptides linked to cytotoxic agents are infused in a manner designed to maximize delivery to the desired location. For example, ricin-linked high affinity angiostatin fragments are delivered through a cannula into vessels supplying the target site or directly into the target. Such agents are also delivered in a controlled manner through osmotic pumps coupled to infusion cannulae. A combination of angiostatin antagonists may be co-applied with stimulators of angiogenesis to increase vascularization of tissue. This therapeutic regimen provides an effective means of destroying metastatic cancer.

Angiostatin may be used in combination with other compositions and procedures for the treatment of diseases. For example, a tumor may be treated conventionally with surgery, radiation or chemotherapy combined with angiostatin and then angiostatin may be subsequently administered to the patient to extend the dormancy of micrometastases and to stabilize any residual primary tumor.

The angiostatin of the present invention also can be used to generate antibodies that are specific for the inhibitor. The antibodies can be either polyclonal antibodies or monoclonal antibodies. These antibodies that specifically bind to the angiostatin or angiostatin receptors can be used in diagnostic methods and kits that are well known to those of ordinary skill in the art to detect or quantify the angiostatin or angiostatin receptors in a body fluid or tissue. Results from these tests can be used to diagnose or predict the occurrence or recurrence of a cancer and other angiogenic mediated diseases.

The angiostatin also can be used in a diagnostic method and kit to detect and quantify antibodies capable of binding angiostatin. These kits would permit detection of circulating angiostatin antibodies which indicates the spread of micrometastases in the presence of angiostatin secreted by primary tumors in situ. Patients that have such circulating anti-angiostatin antibodies may be more likely to develop tumors and cancers, and may be more likely to have recurrences of cancer after treatments or periods of remission. The Fab fragments of these anti-angiostatin antibodies may be used as antigens to generate anti-angiostatin Fab-fragment antisera which can be used to neutralize the removal of circulating angiostatin by anti-angiostatin antibodies.

Another aspect of the present invention is a method of blocking the action of excess endogenous angiostatin. This can be done by passively immunizing a human or animal with antibodies specific for the undesired angiostatin in the system. This treatment can be important in treating abnormal ovulation, menstruation and placentation, and vasculogenesis. This provides a useful tool to examine the effects of angiostatin removal on metastatic processes. The Fab fragment of angiostatin antibodies contains the binding site for angiostatin. This fragment is isolated from angiostatin antibodies using techniques known to those skilled in the art. The Fab fragments of angiostatin antisera are used as antigens to generate production of anti-Fab fragment serum. Infusion of this antiserum against the Fab fragments of angiostatin prevents angiostatin from binding to angiostatin antibodies. Therapeutic benefit is obtained by neutralizing endogenous anti-angiostatin antibodies by blocking the binding of angiostatin to the Fab fragments of anti-angiostatin. The net effect of this treatment is to facilitate the ability of endogenous circulating angiostatin to reach target cells, thereby decreasing the spread of metastases It is to be understood that the present invention is contemplated to include any derivatives of the angiostatin that have endothelial inhibitory activity. The present invention includes the entire angiostatin protein, derivatives of the angiostatin protein and biologically-active fragments of the angiostatin protein. These include proteins with angiostatin activity that have amino acid substitutions or have sugars or other molecules attached to amino acid functional groups. The present invention also includes genes that code for angiostatin and the angiostatin receptor, and to proteins that are expressed by those genes.

The proteins and protein fragments with the angiostatin activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the angiostatin may be incorporated into biodegradable polymers allowing for sustained release of the compound, the polymers being implanted in the vicinity of where drug delivery is desired, for example, at the site of a tumor or implanted so that the angiostatin is slowly released systemically. Osmotic minipumps may also be used to provide controlled delivery of high concentrations of angiostatin through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The dosage of the angiostatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the angiostatin can be administered. Depending upon the half-life of the angiostatin in the particular animal or human, the angiostatin can be administered between several times per day to once a week. It is to be understood that the present invention has application for both human and veterinary use. The methods of the present invention contemplate single as well as multiple administrations, given either simultaneously or over an extended period of time.

The angiostatin formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The angiostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Different peptide fragments of the intact angiostatin molecule can be synthesized for use in several applications including, but not limited to the following; as antigens for the development of specific antisera, as agonists and antagonists active at angiostatin binding sites, as peptides to be linked to cytotoxic agents for targeted killing of cells that bind angiostatin. The amino acid sequences that comprise these peptides are selected on the basis of their position on the exterior regions of the molecule and are accessible for binding to antisera. The amino and carboxyl termini of angiostatin, as well as the mid-region of the molecule are represented separately among the fragments to be synthesized. The amino and carboxyl termini of angiostatin both contain tyrosine and lysine residues and are labeled with many techniques. A tyrosine or lysine is added to fragments that do not have these residues to facilitate labeling of reactive amino and hydroxyl groups on the peptide. These peptide sequences are compared to known sequences using the GenBank, Brookhaven Protein, SWISS-PROT, and PIR databases to determine potential sequence homologies. This information facilitates elimination of sequences that exhibit a high degree of sequence homology to other molecules, thereby enhancing the potential for high specificity in the development of antisera, agonists and antagonists to angiostatin.

Peptides can be synthesized in a standard microchemical facility and purity checked with HPLC and mass spectrophotometry. Methods of peptide synthesis, HPLC purification and mass spectrophotometry are commonly known to those skilled in these arts.

Peptides and angiostatin are also produced in recombinant *E. coli*, as previously described in Example 19 below, or yeast expression systems, and purified with column chromatography.

Angiostatin and angiostatin derived peptides can be coupled to other molecules using standard methods. The amino and carboxyl termini of angiostatin both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Angiostatin peptides are chemically coupled to isotopes, enzymes, carrier proteins, cytotoxic agents, fluorescent molecules and other compounds for a variety of applications. The efficiency of the coupling reaction is determined using different techniques appropriate for the specific reaction. For example, radiolabeling of an angiostatin peptide with $^{125}I$ is accomplished using chloramine T and $Na^{125}I$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted $Na^{125}I$ is separated from the labeled angiostatin peptide. The peptide fractions with the highest specific radioactivity are stored for subsequent use such as analysis of the ability to bind to angiostatin antisera.

Another application of peptide conjugation is for production of polyclonal antisera. For example, angiostatin peptides containing lysine residues are linked to purified bovine serum albumin using glutaraldehyde. The efficiency of the reaction is determined by measuring the incorporation of radiolabeled peptide. Unreacted glutaraldehyde and peptide are separated by dialysis. The conjugate is stored for subsequent use.

Antiserum against angiostatin can be generated. After peptide synthesis and purification, both monoclonal and polyclonal antisera are raised using established techniques known to those skilled in the art. For example, polyclonal antisera may be raised in rabbits, sheep, goats or other animals. Angiostatin peptides conjugated to a carrier molecule such as bovine serum albumin, or angiostatin itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400×g at 4° C. for about 30 minutes. The serum is removed, aliquoted, and stored at 4° C. for immediate use or at −20° to −90° C. for subsequent analysis.

All serum samples from generation of polyclonal antisera or media samples from production of monoclonal antisera are analyzed for determination of titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. Angiostatin peptides are coupled to the gel in the affinity column. Antiserum samples are passed through the column and anti-angiostatin antibodies remain bound to the column. These antibodies are subsequently eluted, collected and evaluated for determination of titer and specificity.

The highest titer angiostatin antisera is tested to establish the following; a) optimal antiserum dilution for highest specific binding of the antigen and lowest non-specific binding, b) the ability to bind increasing amounts of angiostatin peptide in a standard displacement curve, c) potential cross-reactivity with related peptides and proteins, including plasminogen and also angiostatin of related species, d) ability to detect angiostatin peptides in extracts of plasma, urine, tissues, and in cell culture media.

Kits for measurement of angiostatin are also contemplated as part of the present invention. Antisera that possess the highest titer and specificity and can detect angiostatin peptides in extracts of plasma, urine, tissues, and in cell culture media are further examined to establish easy to use kits for rapid, reliable, sensitive, and specific measurement and localization of angiostatin. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. An angiostatin RIA is illustrated below. After successful radioiodination and purification of angiostatin or an angiostatin peptide, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4° C. for 24 hours, protein A is added and the tubes are vortexed, incubated at room temperature for 90 minutes, and centrifuged at approximately 2000–2500×g at 4° C. to precipitate the complexes of antibody bound to labeled antigen. The supernatant is removed by aspiration and the radioactivity in the pellets counted in a gamma counter. The antiserum dilution that binds approximately 10 to 40 % of the labeled peptide after subtraction of the non-specific binding is further characterized.

Next, a dilution range (approximately 0.1 pg to 10 ng) of the angiostatin peptide used for development of the antiserum is evaluated by adding known amounts of the peptide to tubes containing radiolabeled peptide and antiserum. After an additional incubation period, for example, 24 to 48 hours, protein A is added and the tubes centrifuged, supernatant removed and the radioactivity in the pellet counted. The displacement of the binding of radiolabeled angiostatin peptide by the unlabeled angiostatin peptide (standard) provides a standard curve. Several concentrations of other angiostatin peptide fragments, plasminogen, angiostatin from different species, and homologous peptides are added to the assay tubes to characterize the specificity of the angiostatin antiserum.

Extracts of various tissues, including but not limited to primary and secondary tumors, Lewis lung carcinoma, cultures of angiostatin producing cells, placenta, uterus, and other tissues such as brain, liver, and intestine, are prepared using extraction techniques that have been successfully employed to extract angiostatin. After lyophilization or Speed Vac of the tisssue extracts, assay buffer is added and different aliquots are placed into the RIA tubes. Extracts of known angiostatin producing cells produce displacement curves that are parallel to the standard curve, whereas extracts of tissues that do not produce angiostatin do not displace radiolabeled angiostatin from the angiostatin antiserum. In addition, extracts of urine, plasma, and cerebrospinal fluid from animals with Lewis lung carcinoma are added to the assay tubes in increasing amounts. Parallel displacement curves indicate the utility of the angiostatin assay to measure angiostatin in tissues and body fluids.

Tissue extracts that contain angiostatin are additionally characterized by subjecting aliquots to reverse phase HPLC. Eluate fractions are collected, dried in Speed Vac, reconstituted in RIA buffer and analyzed in the angiostatin RIA. The maximal amount of angiostatin immunoreactivity is located in the fractions corresponding to the elution position of angiostatin.

The assay kit provides instructions, antiserum, angiostatin or angiostatin peptide, and possibly radiolabeled angiostatin and/or reagents for precipitation of bound angiostatin-angiostatin antibody complexes. The kit is useful for the measurement of angiostatin in biological fluids and tissue extracts of animals and humans with and without tumors.

Another kit is used for localization of angiostatin in tissues and cells. This angiostatin immunohistochemistry kit provides instructions, angiostatin antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This angiostatin immunohistochemistry kit permits localization of angiostatin in tissue sections and cultured cells using both light and electron microscopy. It is used for both research and clinical purposes. For example, tumors are biopsied or collected and tissue sections cut with a microtome to examine sites of angiostatin production. Such information is useful for diagnostic and possibly therapeutic purposes in the detection and treatment of cancer. This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Another method to visualize sites of angiostatin biosynthesis involves radiolabeling nucleic acids for use in in situ hybridization to probe for angiostatin message.

Example 1

Choice of an animal-tumor system in which growth of metastasis is inhibited by the primary tumor and is accelerated after removal of the primary tumor.

By screening a variety of murine tumors capable of inhibiting their own metastases, a Lewis lung carcinoma was selected in which the primary tumor most efficiently inhibited lung metastasis. Syngeneic C57BI6/J six-week-old male mice were injected (subcutaneous dorsum) with $1\times10^6$ tumor cells. Visible tumors first appeared after 3–4 days. When tumors were approximately 1500 $mm^3$ in size, mice were randomized into two groups. The primary tumor was completely excised in the first group and left intact in the second group after a sham operation. Although tumors from 500 $mm^3$ to 3000 $mm^3$ inhibited growth of metastases, 1500 $mm^3$ was the largest primary tumor that could be safely resected with high survival and no local recurrence.

After 21 days, all mice were sacrificed and autopsied. In mice with an intact primary tumor, there were four +2 visible metastases, compared to fifty +5 metastases in the mice in which the tumor had been removed ($p<0.0001$). These data were confirmed by lung weight, which correlates closely with tumor burden, as has been previously demonstrated. There was a 400% increase in wet lung weight in the mice that had their tumors removed compared to mice in which the tumor remained intact ($p<0.0001$).

This experimental model gave reproducible data and the experiment described is reproducible. This tumor is labeled "Lewis lung carcinoma-low metastatic" (LLC-Low). The tumor also suppressed metastases in a nearly identical pattern in SCID mice, which are deficient in both B and T lymphocytes.

Example 2

Isolation of a variant of Lewis lung carcinoma tumor that is highly metastatic, whether or not the primary tumor is removed.

A highly metastatic variant of Lewis lung carcinoma arose spontaneously from the LLC-Low cell line in one group of mice and has been isolated according to the methods described in Example I and repeatedly transplanted. This tumor (LLC-High) forms more than 30 visible lung metastases whether or not the primary tumor is present.

Example 3

Size of metastases and proliferation rate of tumor cells within them. Effect of the primary tumor that inhibits metastases (LLC-Low).

C57Bl6/J mice were used in all experiments. Mice were inoculated subcutaneously with LLC-Low cells, and 14 days later the primary tumor was removed in half of the mice. At 5, 10 and 15 days after the tumor had been removed, mice were sacrificed. Histological sections of lung metastases were obtained. Mice with an intact primary tumor had micrometastases in the lung which were not neovascularized. These metastases were restricted to a diameter of 12–15 cell layers and did not show a significant size increase even 15 days after tumor removal. In contrast, animals from which the primary tumor was removed, revealed large vascularized metastases as early as 5 days after operation. These metastases underwent a further 4-fold increase in volume by the 15th day after the tumor was removed (as reflected by lung weight and histology). Approximately 50% of the animals who had a primary tumor removed died of lung metastases before the end of the experiment. All animals with an intact primary tumor survived to the end of the experiment.

Replication rate of tumor cells within metastases was determined by counting nuclei stained with BrdU which had been previously injected into the mice. The high percentage of tumor cells incorporating BrdU in small, avascular metastases of animals with an intact primary tumor was equivalent to the BrdU incorporation of tumor cells in the large vascularized metastases of mice from which the primary tumor had been removed (FIG. 3). This finding suggests that the presence of a primary tumor has no direct effect on the replication rate of tumor cells within a metastasis.

In FIG. 3, the left panel shows BrdU labeling index of tumor cells in the lung in the presence or absence of a primary tumor. Before immunohistochemical staining, sections were permeabilized with 0.2M HCl for 10 minutes and digested with 1 μg/ml proteinase K (Boehringer Mannheim GmbH, Mannheim, Germany) in 0.2M Tris-HCl, 2 mM $CaCl_2$ at 37° C. for 15 minutes. Labeling index was estimated by counting percentage of positive nuclei at 250 power. The right panel of FIG. 3 depicts an analysis of total lung weight of tumors with primary tumors intact or removed 5, 10 and 15 days after operation. Animals were sacrificed 6 hours after intraperitoneal injection of BrdU (0.75 mg/mouse).

Example 4

Inhibition of angiogenesis in lung metastases in the presence of an intact primary tumor.

To measure the degree of vascularization in lung metastases, tissues were stained with antibodies against von Willebrand factor (an endothelial specific marker, available from Dako Inc., Carpenteria, Calif.). Metastases from animals with intact tumors formed a thin cuff (8–12 tumor cell layers) around existing pulmonary vessels. Except for the endothelial cells of the vessel lining, no or few cells were positive for von Willebrand factor. In contrast, lung metastases of animals 5 days after removal of the primary tumor were not only larger but were also infiltrated with capillary sprouts containing endothelial cells which stained strongly for von Willebrand factor.

In immunohistochemical analysis of the presence of endothelial cells in lung metastases, a lung metastasis with the primary lung tumor intact 19 days after inoculation, had a cuff of tumor cells around a pre-existing microvessel in the lung. The metastasis was limited to 8 to 12 cell layers. There was no evidence of neovascularization around the microvessel, and it did not contain any new microvessels. This was typical of the maximum size of an avascular pre-angiogenic metastasis.

In an immunohistochemical analysis of tissue collected five days after the primary tumor was resected (19 days after inoculation of the primary tumor), the metastasis surrounded a pre-existing vessel in the lung. In contrast, in the sample where the primary tumor was not resected, the tumor was neovascularized. Thus, an intact primary tumor inhibits formation of new capillary blood vessels in metastases, but proliferation of tumor cells within a metastasis are not affected by the primary tumor.

Example 5

A primary tumor inhibits angiogenesis of a second tumor implanted in the mouse cornea. Growth of this second tumor is inhibited.

A 0.25 to 0.5 $mm^2$ Lewis lung tumor (LLC-Low) was implanted in the mouse cornea on day 0. (Muthukkaruppan Vr., et al., Angiogenesis in the mouse cornea. *Science* 205:1416–1418, 1979) A primary tumor was formed by inoculating $1\times10^6$ LLC-Low cells subcutaneously in the dorsum, either 4 or 7 days before the corneal implant; or on the day of the corneal implant; or 4 or 7 days after the corneal implant. Control mice received the corneal implant but not the subcutaneous tumor. Other control mice received the corneal implant and an inoculation of LLC-High tumor cells in the dorsum 4 days before the corneal implant. The corneas were evaluated daily by slit-lamp stereomicroscopy for the growth of the corneal tumor (measured by an ocular micrometer) and for the growth of new capillary vessels from the edge of the corneal limbus.

In control mice not bearing a primary subcutaneous tumor, a majority of corneas (6/8) developed neovascularization starting at day 6 to 7 days after corneal implantation and continuing to day 10. By day 10, the vascularized corneal tumors had reached approximately a quarter of the volume of the whole eye. In the presence of the primary subcutaneous LLC-Low tumor, the corneal implants did not become vascularized if the primary tumor was in place by at least 4 days or more before the corneal implant (Table 1). In the absence of neovascularization, corneal tumors grew slowly as thin, white, avascular discs within the cornea.

However, if the primary tumor was not implanted until 4 days after the corneal implant, corneas became vascularized and 3/3 corneal tumors grew at similar rates as the non-tumor bearing controls. In the presence of the primary subcutaneous LLC-High tumor, the majority of corneas (2/3) developed neovascularization starting at day 7 after corneal implantation and continuing to day 10. By day 10, the vascularized corneal tumors again had reached approximately a quarter of the volume of the whole eye.

TABLE 1

Inhibition of tumor angiogenesis in the cornea by a primary subcutaneous tumor. [All primary tumors are LLC-Low except (*) which is LLC-High].

| Day of eye implant | 0 | 0 | 0 | 0 | 0 | 0 | 0 |
|---|---|---|---|---|---|---|---|
| Day of primary tumor implant | −7 | −4 | −4* | 0 | none | +4 | +7 |
| Number of mice with new corneal vessels at day 10 | 2/10 | 0/9 | 2/3 | 2/3 | 6/8 | 3/3 | 2/3 |

It would be expected that 0/10 corneas would show neovascularization when the primary LLC-Low subcutaneous tumor was implanted 7 days before the eye tumor implant (i.e. −7). However, 2 of the tumors (2/10) had become necrotic because they were too large (>3 $cm^3$).

Example 6

Primary intact tumor inhibits angiogenesis induced by a secondary subcutaneous implant of basic fibroblast growth factor (bFGF.).

Although the experiments described in Examples 4 and 5 show that a primary tumor inhibits angiogenesis in a secondary metastasis, these studies do not reveal whether the primary tumor: (i) inhibits endothelial proliferation (or angiogenesis) directly, or (ii) indirectly by down-regulating the angiogenic activity of the metastatic tumor cells. To distinguish between these two possibilities, a focus of subcutaneous angiogenesis was induced by an implant of matrigel containing basic fibroblast growth factor (bFGF). (Passaniti A, et al., A simple, quantitative method for assessing angiogenesis and anti-angiogenic agents using reconstituted basement membrane, heparin and fibroblast growth factor. *Lab. Invest.* 67:519, 1992)

Matrigel (an extract of basement membrane proteins), containing either 25 or 50 ng/ml bFGF in the presence of heparin, was injected subcutaneously on the ventral surface of normal and tumor-bearing mice (LLC-Low). Mice were sacrificed 4 days later and hemoglobin concentration in the gel was measured to quantify blood vessel formation. It has previously been shown that the number of new vessels which enter the matrigel is correlated with hemoglobin concentration. (Folkman J., Angiogenesis and its inhibitors in "*Important Advances in Oncology* 1985", V T DeVita, S. Hellman and S. Rosenberg, editors, J. B. Lippincott, Philadelphia 1985) Some gels were also prepared for histological examination. In normal mice, matrigel pellets which contained 50 ng/ml bFGF were completely red. They were heavily invaded by new capillary vessels, and contained 2.4 g/dl hemoglobin. Matrigel which lacked bFGF was translucent and gray and contained only 0.4 g/dl hemoglobin (a 6-fold difference). In contrast, matrigel from mice with a primary tumor contained only 0.5 g/dl (FIG. 4).

The near complete inhibition of angiogenesis in this experiment suggests that the presence of a Lewis lung primary tumor can inhibit bFGF-induced angiogenesis directly.

Example 7

Transfer of serum from a tumor-bearing animal to an animal from which the primary tumor has been removed suppresses metastases.

Mice were implanted with Lewis lung carcinoma as described above. After 15 days, when tumors were approximately 1500 $mm^3$, the mice were randomized into four groups. Three groups underwent complete surgical resection of the primary tumor; in one group the tumors were left in place (after a sham surgical procedure). The mice in the three resection groups then received daily intraperitoneal injections of saline, serum from normal nontumor bearing mice, or serum from mice with 1500 $mm^3$ Lewis lung carcinomas. The group of mice with the tumors left intact received intraperitoneal saline injections. All mice were treated for 21 days, after which the animals were euthanized and lung metastases were counted (Table 2).

TABLE 2

| | Primary Tumor Removed | | | Primary Tumor Intact |
|---|---|---|---|---|
| Treatment (Intraperitoneal Injections) | Saline | Serum from normal mice | Serum from tumor-bearing mice | Saline Injections |
| Number of Lung Metastases: | 55 ± 5 | 50 ± 4 | 7 ± 2 | 3 ± 1 |

These results were confirmed by lung weight. p=<0.0001 for the difference between the two groups [(55 & 50) vs. (7 & 3)]. Similar results have been obtained using angiostatin from the urine of tumor-bearing animals.

Example 8

Bovine capillary endothelial (BCE) cell assay

BCE cells are used between passages 9 and 14 only. At day 0, BCE cells are plated onto gelatinized (1.5% gelatin in PBS at 37°, 10% $CO_2$ for 24 hours and then rinsed with 0.5 ml PBS) 24 well plates at a concentration of 12,500 cells/well. Cell counts are performed using a hemocytometer. Cells are plated in 500 µl DMEM with 10% heat-inactivated (56° C. for 20 minutes) bovine calf serum and 1% glutamine-pen-strep (GPS).

BCE cells are challenged as follows: Media is removed and replaced with 250 µl of DMEM/5% BCS/1%GPS. The sample to be tested is then added to wells. (The amount varies depending on the sample being tested) Plates are placed at 37° C./10% $CO_2$ for approximately 10 minutes. 250 µl of DMEM/5% BCS/1% GPS with 2 ng/ml bFGF is added to each well. The final media is 500 µl of DMEM/5% BCS/1%GPS/with 1 ng/ml bFGF. The plate is returned to 37° C./10% $CO_2$ incubator for 72 hours.

At day 4, cells are counted by removing the medium and then trypsinizing all wells (0.5 ml trypsin/EDTA) for 2 to 3 minutes. The suspended cells are then transferred to scintillation vials with 9.5 ml Hemetall and counted using a Coulter counter A unit of activity is that amount of serum containing angiostatin that is capable of producing half-maximal inhibition of capillary endothelial proliferation when endothelial cells are incubated in bFGF 1 ng/ml for 72 hours.

Example 9

Serum from mice bearing the low metastatic Lewis lung tumor (LLC-Low) inhibits capillary endothelial cell proliferation in vitro.

Bovine capillary endothelial cells were stimulated by basic fibroblast growth factor (bFGF 1 ng/ml), in a 72-hour proliferation assay. The serum of tumor-bearing mice added to these cultures inhibited endothelial cell proliferation in a dose-dependent and reversible manner. Normal serum was not inhibitory (FIG. 5). Endothelial cell proliferation was inhibited in a similar manner (relative to controls) by serum obtained from tumor-bearing nu/nu mice and SCID mice. After the primary tumor was removed, angiostatin activity disappeared from the serum by 3–5 days.

Tumor-bearing serum also inhibited bovine aortic endothelial cells and endothelial cells derived from a spontaneous mouse hemangioendothelioma, (Obeso, et al., "Methods in Laboratory Investigation, A Hemangioendothelioma-derived cell line; Its use as a Model for the Study of Endothelial Cell Biology," *Lab Invest.*, 63(2), pgs 259–269, 1990) but did not inhibit Lewis lung tumor cells, 3T3 fibroblasts, aortic smooth muscle cells, mink lung epithelium, or W138 human fetal lung fibroblasts.

Example 10

Serum from mice bearing the Lewis lung tumor (LLC-High) that does not inhibit metastases, does not inhibit capillary endothelial cell proliferation in vitro.

Serum from mice bearing a primary tumor of the LLC-High did not significantly inhibit proliferation of bFGF-stimulated bovine capillary endothelial cells relative to controls. Also, when this serum was subjected to the first two steps of purification (heparin-Sepharose chromatography and gel filtration), angiostatin activity was not found in any fractions.

Example 11

Ascites from Lewis lung carcinoma (low metastatic), also generates angiostatin serum.

Mice received intraperitoneal injections of either LLC-Low or LLC-High tumor cells ($10^6$), and one week later, 1–2 ml of bloody ascites was obtained from each of 10–20 mice. Mesenteric tumor seeding was seen. The mice were then euthanized. Serum was obtained by cardiac puncture. Serum was also obtained from normal, non-tumor-bearing mice as a control. Serum and ascites were centrifuged to remove cells, and the supernate was assayed on bovine capillary endothelial cells stimulated by bFGF (1 ng/ml) (see Example 8). Ascites originating from both tumor types stimulated significant proliferation of capillary endothelial cells (e.g., 100% proliferation) over controls after 72 hours (FIG. 6). In contrast, serum from the low metastatic mice inhibited endothelial cell proliferation (inhibition to 79% of controls). The serum from the high metastatic line was stimulatory by 200%.

These data show that the ascites of the low metastatic line contains a predominance of endothelial growth stimulator over angiostatin. This condition is analogous to a solid primary tumor. Furthermore, angiostatin activity appears in the serum, as though it were unopposed by stimulatory activity. This pattern is similar to the solid primary tumor (LLC-Low). The ascites from the high metastatic tumor (LLC-High) also appears to contain a predominance of endothelial cell stimulator, but angiostatin cannot be identified in the serum.

Example 12

Fractionation of angiostatin from serum by column chromatography and analysis of growth-inhibitory fractions by SDS-PAGE.

To purify the angiostatin(s), serum was pooled from tumor-bearing mice. The inhibitory activity, assayed according the above-described in vitro inhibitor activity assay, was sequentially chromatographed using heparin-Sepharose, Biogel AO.5 mm agarose, and several cycles of C4-reverse phase high performance liquid chromatography (HPLC). SDS-PAGE of the HPLC fraction which contained endothelial inhibitory activity, revealed a discrete band of apparent reduced $M_r$ of 38,000 Daltons, which was purified approximately 1 million-fold (see Table 3) to a specific activity of approximately $2\times10^7$. At different stages of the purification, pooled fractions were tested with specific antibodies for the presence of known endothelial inhibitors. Platelet factor-4, thrombospondin, or transforming growth factor beta, were not found in the partially purified or purified fractions.

TABLE 3

| | Specific activity (units*/mg) | Fold purification |
|---|---|---|
| Serum | 1.69 | 1 |
| Heparin Sepharose | 14.92 | 8.8 |
| Bio-gel AO.5m | 69.96 | 41.4 |
| HPLC/C4 | $2 \times 10^7$ | $1.2 \times 10^6$ |

*A unit of activity is that amount of serum containing angiostatin that is capable of producing half-maximal inhibition of capillary endothelial proliferation when endothelial cells are incubated in bFGF 1 ng/ml for 72 hours.

Example 13

Fractionation of angiostatin from urine by column chromatography and analysis of growth-inhibitory fractions by SDS-PAGE.

Purification of the endothelial cell inhibitor(s) from serum is hampered by the small volume of serum that can be obtained from each mouse and by the large amount of protein in the serum.

Urine from tumor bearing mice was analyzed and found that it contains an inhibitor of endothelial cell proliferation that is absent from the urine of non-tumor bearing mice and from mice with LLC-high tumors. Purification of the endothelial cell inhibitory activity was carried out by the same strategy that was employed for purification of serum (described above) (FIG. 7).

FIG. 7 shows C4 reverse phase chromatography of partially purified serum or urine from tumor-bearing animals. All fractions were assayed on bovine capillary endothelial cells with bFGF in a 72-hour proliferation assay as described in Example 8. A discrete peak of inhibition was seen in both cases eluting at 30–35% acetonitrile in fraction 23. SDS-polyacrylamide gel electrophoresis of inhibitory fraction from the third cycle of C4 reverse phase chromatography of serum from tumor-bearing animals showed a single band at about 38,000 Daltons.

Example 14

Characterization of circulating angiostatin.

Endothelial inhibition was assayed according to the procedure described in Example 9. Angiostatin was isolated on a Synchropak HPLC C4 column. (Synchrom, Inc. Lafayette, Ind. The inhibitor was eluted at 30 to 35% acetonitrile gradient. On a sodium dodecyl sulfate polyacrylamide gel electrophoresis (PAGE) gel under reducing conditions (β-mercaptoethanol(5% v/v), the protein band with activity eluted at 38 kilodaltons. Under non-reducing conditions, the protein with activity eluted at 28 kilodaltons. The activity is found at similar points whether the initial sample was isolated from urine or from serum. Activity was not detected with any other bands.

Activity associated with the bands was lost when heated (100° C. for 10 minutes) or treated with trypsin. When the band with activity was extracted with a water/chloroform mixture (1:1), the activity was found in the aqueous phase only.

Example 15

Purification of inhibitory fragments from human plasminogen:

Plasminogen lysine binding site I was obtained from Sigma Chemical Company. The preparation is purified human plasminogen after digestion with elastase. Lysine binding site I obtained in this manner is a population of peptides that contain, in aggregate, at least the first three triple-loop structures (numbers 1 through 3) in the plasmin A-chain (Kringle 1+2+3). (Sotrrup-Jensen, L., et al. in *Progress in Chemical Fibrinolysis and Thrombolysis*, Vol. 3, 191, Davidson, J. F., et al. eds. Raven Press, New York 1978 and Wiman, B., et al., *Biochemica et Biophysica Acta*, 579, 142 (1979)). Plasminogen lysine binding site I (Sigma Chemical Company, St. Louis, Mo.) was resuspended in water and applied to a C4-reversed phase column that had been equilibrated with HPLC-grade water/0.1% TFA. The column was eluted with a gradient of water/0.1% TFA to acetonitrile/0.1% TFA and fractions were collected into polypropylene tubes. An aliquot of each was evaporated in a speed vac, resuspended with water, and applied to BCEs in a proliferation assay. This procedure was repeated two times for the inhibitory fractions using a similar gradient for elution. The inhibitory activity eluted at 30–35% acetonitrile in the final run of the C4 column. SDS-PAGE of the inhibitory fraction revealed 3 discrete bands of apparent reduced molecular mass of 40, 42.5, and 45 kd. SDS-PAGE under non-reducing conditions revealed three bands of molecular mass 30, 32.5, and 35 kd respectively.

Example 16

Extraction of inhibitory activity from SDS-PAGE

Purified inhibitory fractions from human plasminogen based purifications were resolved by SDS-PAGE under non-denaturing conditions. Areas of the gel corresponding to bands seen in neighboring lanes loaded with the same samples by silver staining were cut from the gel and incubated in 1 ml of phosphate buffered saline at 4° C. for 12 hours in polypropylene tubes. The supernatant was removed and dialyzed twice against saline for 6 hours (MWCO= 6–8000) and twice against distilled water for 6 hours. The dialysate was evaporated by vacuum centrifugation. The product was resuspended in saline and applied to bovine capillary endothelial cells stimulated by 1 ng/ml basic fibroblast growth factor in a 72 hour assay. Protein extracted from each of the three bands inhibited the capillary endothelial cells.

Example 17

Plasminogen Fragment Treatment Studies

Mice were implanted with Lewis lung carcinomas and underwent resections when the tumors were 1500–2000 $mm^3$. On the day of operation, mice were randomized into 6 groups of 6 mice each. The mice received daily intraperitoneal injections with the three purified inhibitory fragments of human plasminogen, whole human plasminogen, urine from tumor-bearing animals, urine from normal mice, or saline. One group of tumor-bearing animals that had only a sham procedure was treated with saline injections. Immediately after removal of the primary tumor, the mice receive an intraperitoneal injection of 24 μg (1.2 mg/kg/day/mouse) of the inhibitory plasminogen fragments as a loading dose. They then receive a daily intraperitoneal injections of 12 μg of the inhibitory fragment (0.6 mg/kg/day/mouse) for the duration of the experiment. Control mice receive the same dose of the whole plasminogen molecule after tumor removal. For the urine treatments, the urine of normal or tumor bearing mice is filtered, dialyzed extensively, lyophilized, and then resuspended in sterile water to obtain a 250 fold concentration. The mice are given 0.8 ml of the dialyzed urine concentrate, either from tumor bearing mice or normal mice, in two intraperitoneal injections on the day of removal of the primary tumor as a loading dose. They then receive daily intraperitoneal injections of 0.4 ml of the dialyzed and concentrated urine for the course of the experiment. Treatments were continued for 13 days at which point all mice were sacrificed and autopsied.

Figure 9:
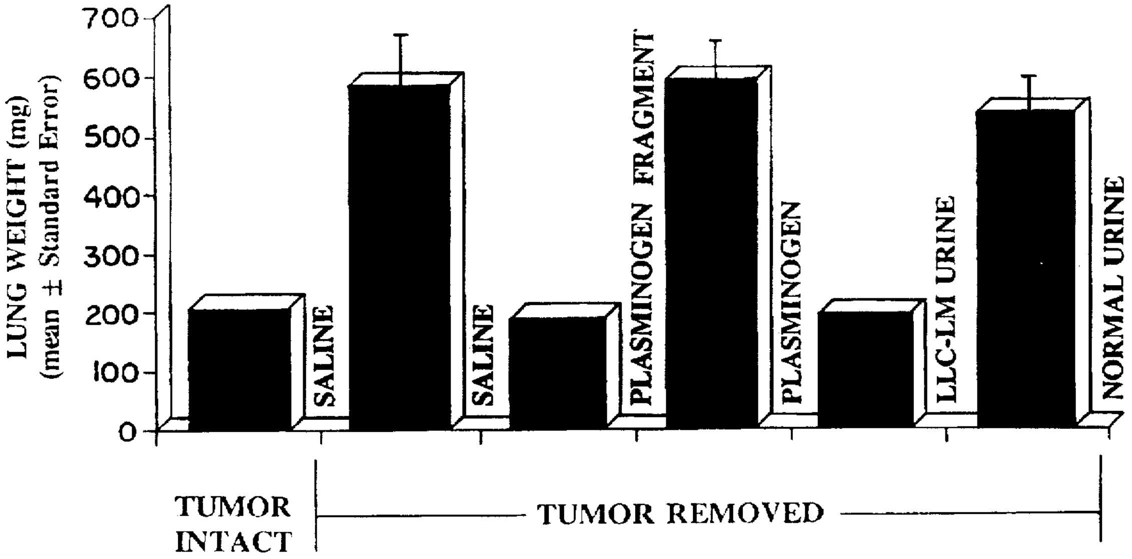
FIG. 9 shows lung weight after the 13 day treatment of mice with intact plasminogen molecule of human plasminogen, active fraction from lysine binding site I preparation, concentrated urine from tumor bearing mice and concentrated urine from normal mice.

The results of the experiment are shown in FIGS. 8 and 9. FIG. 8 shows surface lung metastases after the 13 day treatment. Surface lung metastases refers to the number of metastases seen in the lungs of the mice at autopsy. A stereomicroscope was used to count the metastases. FIG. 7 shows the mean number of surface lung metastases that was counted and the standard error of the mean. As shown, the group of mice with the primary tumor present showed no metastases. The mice in which the primary tumor was resected and were treated with saline showed extensive metastases. The mice treated with the human derived plasminogen fragment showed no metastases. The mice treated with whole plasminogen showed extensive metastases indicating that the whole plasminogen molecule has no endothelial inhibitory activity. Those mice treated with dialyzed and concentrated urine from tumor bearing mice showed no metastases. Mice treated with concentrated urine from normal mice showed extensive metastases. When the weight of the lung was measured, similar results were obtained (FIG. 9).

Example 18

Amino acid sequence of murine and human angiostatin.

The amino acid sequence of angiostatin isolated from mouse urine and angiostatin isolated from the human lysine binding site I fragment preparation was determined on an Applied Biosystem Model 477A protein sequencer. Phenylthiohydantoin amino acid fractions were identified with an on-line ABI Model 120A HPLC. The amino acid sequence determined from the N-terminal sequence and the tryptic digests of the murine and human angiostatin indicate that the sequence of the angiostatin is similar to the sequence beginning at amino acid number 98 of murine plasminogen. Thus, the amino acid sequence of the angiostatin is a molecule comprising a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The beginning amino acid sequence of the murine angiostatin (SEQ ID NO:2) is shown in FIG. 1. The length of the amino acid sequence may be slightly longer or shorter than that shown in the FIG. 1.

N terminal amino acid analysis and tryptic digests of the active fraction of human lysine binding site I (See Example 15) show that the sequence of the fraction begins at approximately amino acid 97 or 99 of human plasminogen and the human angiostatin is homologous with the murine angiostatin. The beginning amino acid sequence of the human angiostatin (starting at amino acid 98) is shown in FIG. 2, (SEQ ID NO:3). The amino acid sequence of murine and human angiostatin is compared in FIG. 2 to corresponding internal amino acid sequences from plasminogen of other species including porcine, bovine, and Rhesus monkey plasminogen, indicating the presence of angiostatin in those species.

Example 19

Expression of human angiostatin in *E. coli*.

The pTrcHisA vector (Invitrogen) was used to obtain high-level, regulated transcription from the trc promoter for enhanced translation efficiency of eukaryotic genes in *E. coli*. Angiostatin is expressed fused to an N-terminal nickel-binding poly-histidine tail for one-step purification using metal affinity resins. The enterokinase cleavage recognition site in the fusion peptide allows for subsequent removal of the N-terminal histidine fusion peptide from the purified recombinant protein.

Figure 10:
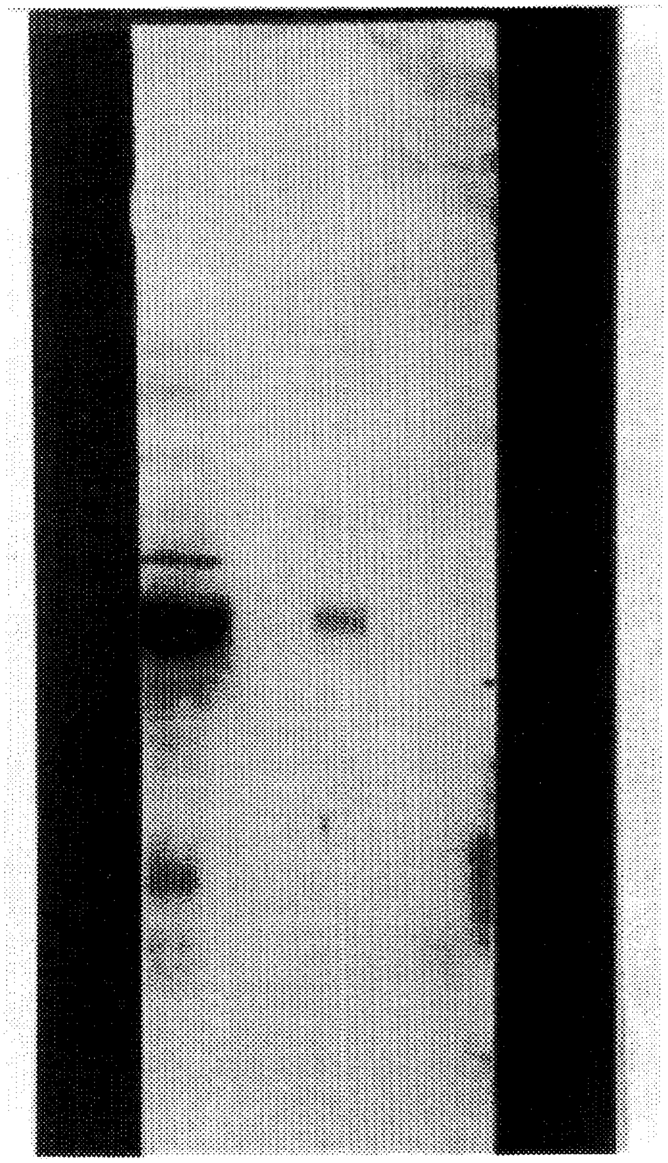
FIG. 10 shows the production of a gene fragment of 1131 base pairs encoding human angiostatin following reverse transcription and amplification using the polymerase chain reaction.

To construct the insert, the gene fragment encoding human angiostatin is obtained from human liver mRNA which is reverse transcribed and amplified using the polymerase chain reaction (PCR) and specific primers. The product of 1131 base pairs encodes amino acids 93 to 470 of human plasminogen (FIG. 10). The amplified fragment was cloned into the XhoI/KpnI site of pTrcHisA. A control construct was made with an irrelevant protein (Malaria, *Plasmodium falciparum*) in place of the gene encoding angiostatin. Both clones were purified identically.

Expressing colonies were selected in the following manner. Colony lifts of *E. coli* transformed with the gene encoding angiostatin were grown on IPTG impregnated nitrocellulose filters and overlaid on an LB agar plate. Following IPTG induction of expression, colonies were lysed on nitrocellulose filters. The nitrocellulose lifts were blocked, rinsed and probed with two separate monoclonal antibodies (mAbs Dcd and Vap; gift of S. G. McCance and F. J. Castellino, University of Notre Dame) which recognize specific conformations of angiostatin. Strongly expressing colonies recognized by the mAbs were selected.

To identify the optimal time for maximal expression, cells were collected at various times before and after IPTG induction and exposed to repeated freeze-thaw cycles, followed by analysis with SDS-PAGE, immunoblotting and probing with mAbs Dcd and Vap.

Expressed protein was purified using a modification of the method of Gross et al. Following resuspension of the pellet, the mixture was stirred, sonicated, and centrifuged through several cycles. Following extensive dialysis and additional purification steps, the expressed protein was examined on an immunoblot using the conformationally-dependent mAbs.

Example 20

Treatment of primary tumors with angiostatin in vivo.

Angiostatin was purified from human plasminogen by limited elastase digestion as described in Example 15 above. Angiostatin was resuspended in phosphate-buffered saline for administration into six week old male C57Bl6/J mice. Animals were implanted subcutaneously with $1\times10^6$ tumor cells of either the Lewis lung carcinoma or T241 fibrosarcoma. Treatment with angiostatin is begun after four days when tumors are 80–160 $mm^3$ in size. Mice received angiostatin injections in either a single injection of 40 mg/kg or two 80 mg/kg injections via intraperitoneal (ip) or subcutaneous (sc) routes. Animals were sacrificed at various times after treatment extending to 19 days.

Figure 11:
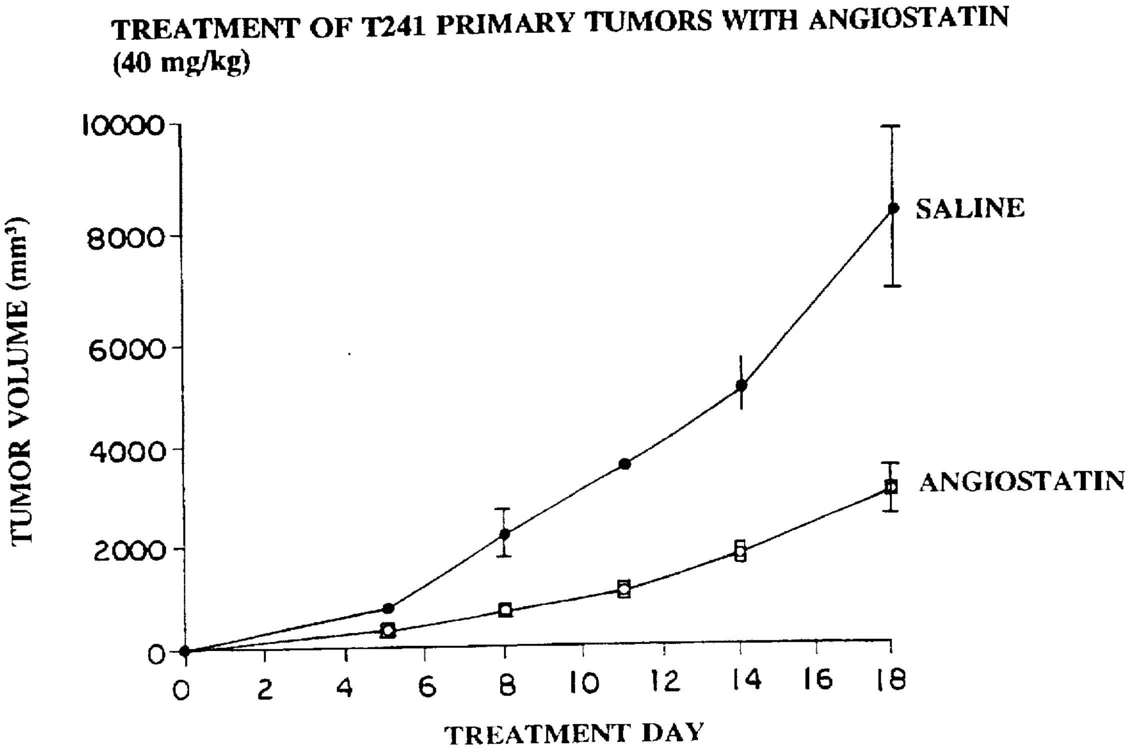
FIG. 11 shows the inhibition of growth of a T241 primary tumor in mice by treatment with human angiostatin in vivo with a single injection of 40 mg/kg/day.

Angiostatin, administered at a daily dose of 40 mg/kg ip, produced a highly significant inhibition of the growth of T241 primary tumors (FIG. 11). This inhibitory effect on growth was visibly evident within 2 days and increased in magnitude throughout the time course of the study. By day 18, angiostatin-treated mice had tumors that were approximately 38% of the volume of the saline injected controls. This difference was statistically significant ($p<0.001$, Students t-test).

Figure 12:
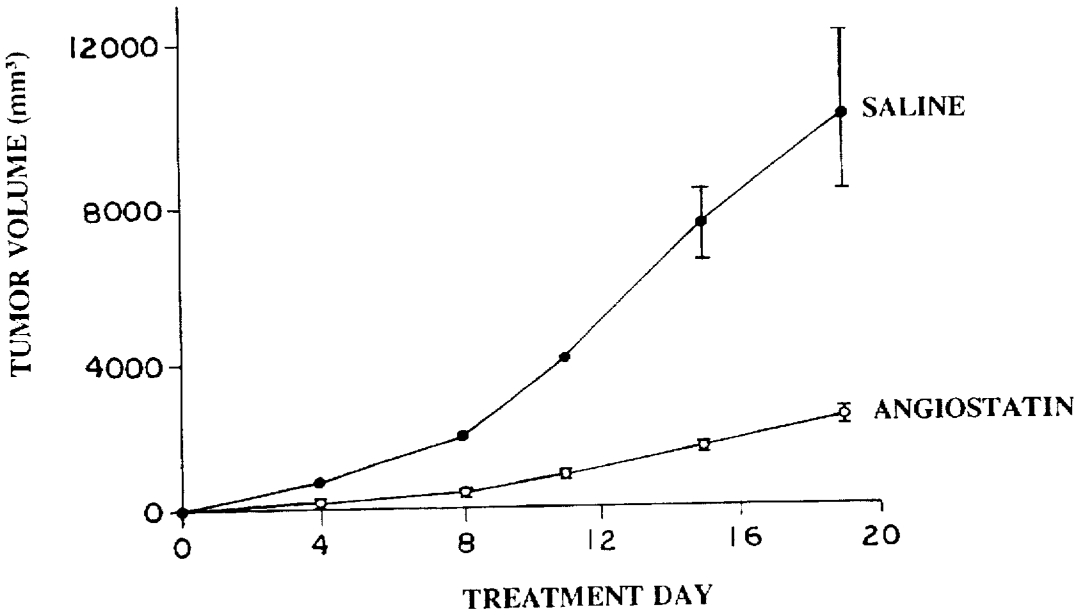
FIG. 12 shows the inhibition of growth of a LLC-LM primary tumor in mice by treatment with human angiostatin in vivo at two doses of 40 mg/kg per dose (80 mg/kg/day).

Angiostatin treatment (total dose of 80 mg/kg/day, administered twice daily at 40 mg/kg ip or sc) also significantly reduced the growth rate of LLC-LM primary tumors (FIG. 12). This inhibitory effect was evident at 4 days and increased in magnitude at all subsequent times examined. On the last day of the experiment (day 19), angiostatin-treated mice possessed a mean tumor volume that was only 20% of the saline-injected controls which was significantly different ($p<0.001$ Students t-test).

These results demonstrate that angiostatin is an extremely potent inhibitor of the growth of two different primary tumors in vivo.

Example 21

Angiostatin maintains dormancy of micrometastases by increasing the rate of apoptosis.

Figure 13:
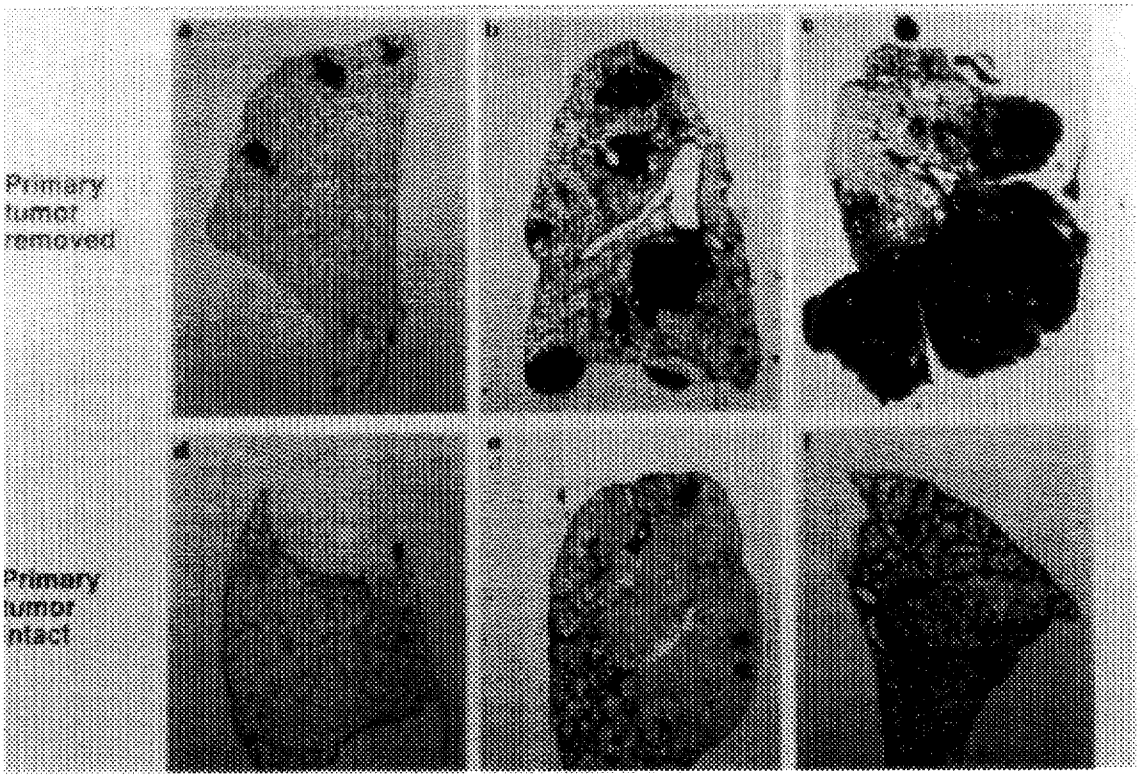
FIG. 13 shows the effect of removal of Lewis lung carcinoma primary tumor on the growth of its lung metastases. Panels 13*a*, 13*b* and 13*c* show growth of lung metastases after removal of a primary tumor. Panels 13*d*, 13*e* and 13*f* show suppression of metastatic growth when the primary tumor is left intact. Animals were killed 5 days (panels 13*a* and 13*d*), 10 days (panels 13*b* and 13*e*) and 15 days (panels 13*c* and 13*f*) after operation. Note the presence of micrometastases (arrows) in the lungs of mice shown in panels 13*d*, 13*e* and 13*f*. Scale bar, 1 mm.

Following subcutaneous inoculation of C57 BL6/J mice with Lewis lung carcinoma cells ($1\times10^6$), primary tumors of approximately 1.5 $cm^3$ developed. Animals were subject to either surgical removal of the primary tumor or sham surgery. At 5, 10 and 15 days after surgery, mice were sacrificed and their lungs prepared for histological examination. Animals with resected primary tumors showed massive proliferation of micrometastases compared to sham operated controls (FIG. 13). These changes were accompanied by a significant increase in lung weight.

Figure 14A:
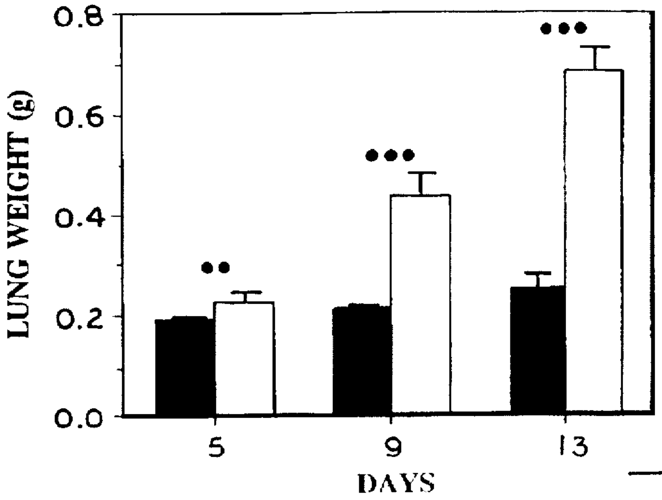
FIG. 14 shows an analysis of the lung weight (panel 14*a*), BrdU labeling index (panel 14*b*) and apoptotic index (panel 14*c*) of metastases in the lungs of mice with the primary Lewis lung tumor intact (solid bars) or removed (blank bars).
Figure 14B:
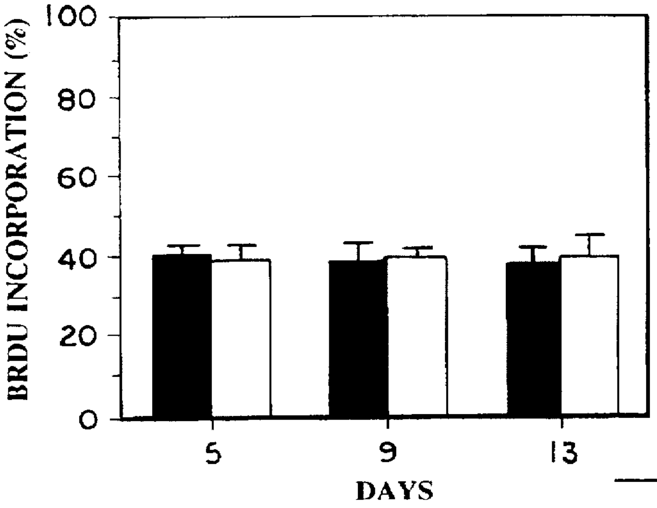
Figure 14C:
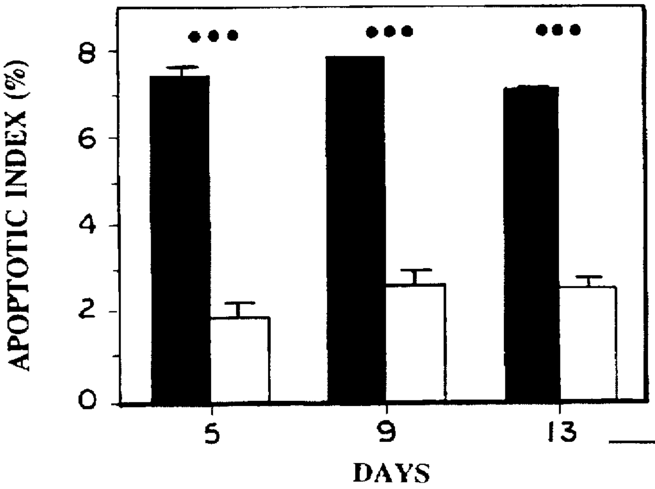

Analysis of tumor cell proliferation, as measured by uptake of bromo-deoxyuridine (BrdU) showed no differences between animals with intact primary tumors or resected tumors at 5, 9 and 13 days, indicating that the increase in tumor mass could not be explained by increased proliferation (FIG. 14). Accordingly, cell death was examined in these animals. Apoptosis, a process of cell death that is dependent on changes in gene expression and accounts for elimination of cells during development and in rapidly proliferating tissues such as the small intestine, was examined by immunohistochemically labeling fragmented DNA with the terminal deoxynucleotidyl transferase (TdT) technique. The apoptotic index was determined at each time of sacrifice. The removal of primary tumors caused a statistically significant increase (approximately 3 to 4 fold) in the apoptotic index at all times examined (FIG. 14).

Figure 15A:
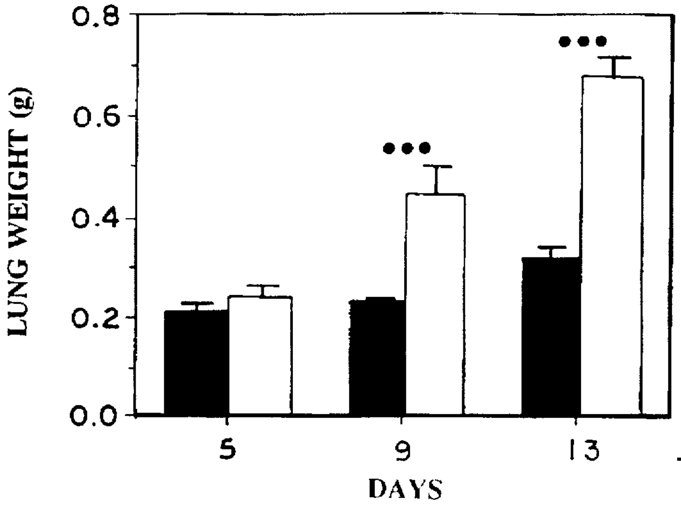
FIG. 15 shows an analysis of the lung weight (panel 15*a*), BrdU labeling index (panel 15*b*) and apoptotic index (panel 15*c*) of metastases in the lungs of mice with removed primary Lewis lung tumors treated with TNP-1470 (solid bars) or saline (blank bars).
Figure 15B:
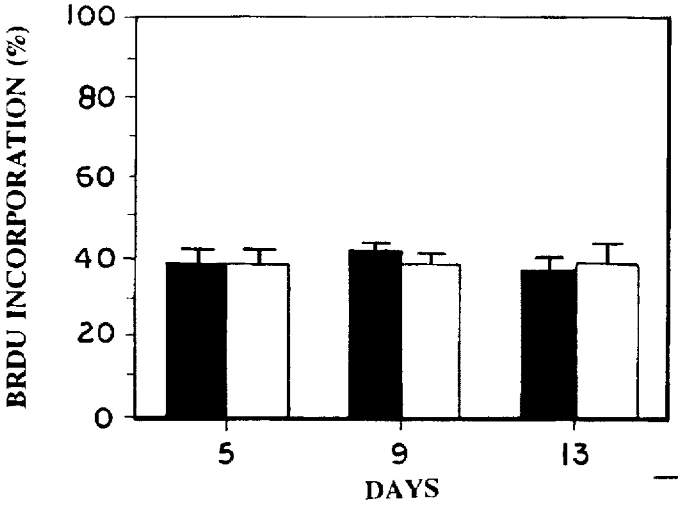
Figure 15C:
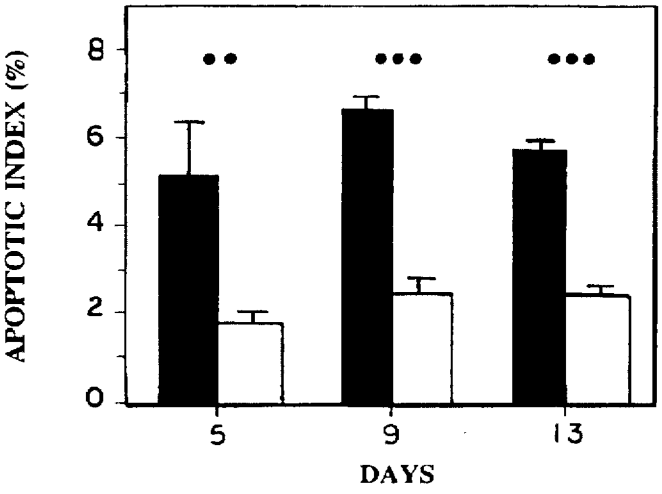

Supporting evidence was obtained by treating mice with removed primary tumors with an exogenous suppressor of angiogenesis. This substance, TNP-1470 (O-chloroacetylcarbamoyl fumagillol, previously named AGM-1470), is an analogue of fumagillin with reported anti-angiogenic activity. Subcutaneous injection of TNP-1470 (30 mg/kg every two days) produced results that were strikingly similar to those described above for animals that had intact primary tumors. These animals displayed a lower lung weight, equivalent proliferative index and increased apoptotic index compared to saline-injected controls (FIG. 15).

These data indicate that metastases remain dormant when tumor cell proliferation is balanced by an equivalent rate of cell death. The removal of the primary tumor causes a rapid increase in the growth of metastases, probably due to the removal of angiogenesis inhibitors (angiostatin) which control metastatic growth by increasing apoptosis in tumor cells. These effects are similar to those seen following removal of primary tumors and administration of an exogenous inhibitor of angiogenesis. Taken together, these data suggest that the primary tumor releases angiostatin which maintains dormancy of micrometastases.

It should be understood, of course, that the foregoing relates only to preferred embodiments of the present invention and that numerous modifications or alterations may be made therein without departing from the spirit and the scope of the invention as set forth in the appended claims.

We claim:

1. A composition comprising, an isolated nucleotide molecule having a sequence that codes for angiostatin protein containing approximately kringle region 1 through 4 of a plasminocen molecule, the angiostatin protein having anti-angiogenic activity, and having a molecular weight of between approximately 38 and 45 kilodaltons as determined by reducing polyacrylamide gel electrophoresis.

2. The composition of claim 1, wherein the nucleotide sequence codes for an amino acid sequence substantially similar to that of a plasminogen fragment beginning at approximately amino acid 98 of a plasrninogen molecule.

3. The composition of claim 1, wherein the nucleutide sequence codes for a protein having a beginning amino acid sequence substantially similar to SEQ ID NO:2.

4. The composition of claim 1, wherein the nucleotide sequence codes for a protein having a beginning amino acid sequence selected from the group consisting of SEQ ID NO:2, SEQ ID NO:3, SEQ ID NO:4, SEQ ID NO:5, and SEQ ID NQ:6.

5. The composition of claim 1, wherein the angiostatin protein has in vitro endothelial cell proliferation inhibiting activity.

6. The composition of claim 1, wherein the angiostatin protein is capable of inhibiting the growth of a cancer.

7. The composition of claim 6, wherein the cancer is selected from the group consisting of a prostate cancer, a breast cancer, a colon cancer, and a lung cancer.

8. The composition of claim 1, further comprising, a vector comprising the nucleotide sequence encoding angiostatin protein, wherein the vector is capable of expressing angiostatin protein when present in a cell.

9. The composition of claim 8, wherein the vector is present in the cell.

10. A composition comprising, an isolated nucleotide molecule having a sequence that codes for angiostatin protein having anti-angiogenic activity, and wherein the anziostatin protein contains approximately kringle regions 1 through 4 of a plasminogen molecule.

11. The composition of claim 10, wherein the nucleotide sequence codes for an amino acid sequence substantially similar to that of an angiostatin protein beginning at approximately amino acid 98 of a plasninogen molecule.

12. The composition of claim 10, wherein the nucleotide sequence codes for a a beginning amino acid sequence substantially similar to SEQ ID NO:2.

13. The composition of claim 10, wherein the nucleotide sequence codes for a beginning amino acid sequence selected from the group consisting of SEQ ID NO:2, SEQ ID NO:3, SEQ ID NO:4, SEQ ID NO:5, and SEQ ID NO:6.

14. The composition of claim 10, wherein the angiostatin protein has endothelial cell proliferation inhibiting activity.

15. The composition of claim 10, wherein the angiostatin protein is capable of inhibiting the growth of a cancer.

16. The composition of claim 15, wherein the cancer is selected from the group consisting of a prostate cancer, a breast cancer, a colon cancer, and a lung cancer.

17. The composition of claim 10, further comprising, a vector comprising the nucleotide sequence encoding angiostatin protein, wherein the vector is capable of expressing angiostatin protein when present in a cell.

18. The composition of claim 17, wherein the vector is present in the cell.

19. A composition comprising, an isolated nucleotide molecule having a sequence that codes for angiostatin protein having a molecular weight of between approximately 38 and 45 kilodaltons as determined by reducing polyacrylamide gel electrophoresis, having anti-angiogenic activity, and having an amino acid sequence substantially similar to a plasminogen fragment beginning at about amino acid 98 of a plasminogen molecule.

20. The composition of claim 19, wherein the nucleotide sequence codes for a protein having a beginning amino acid sequence substantially similar to SEQ ID NO:2.

21. The composition of claim 19, wherein the nucleotide sequence codes for a protein having a beginning amino acid sequence selected from the group consisting of SEQ ID NO:2, SEQ ID NO:3, SEQ ID NO:4, SEQ ID NO:5 ad SEQ ID NO:6.

22. The composition of claim 19, wherein the angiostatin protein has in vitro endothelial cell proliferation inhibiting activity.

23. The composition of claim 19, wherein the angiostatin protein is capable of inhibiting the growth of cancer.

24. The composition of claim 23, wherein the cancer is selected from the group consisting of a prostate cancer, a breast cancer, a colon cancer and a lung cancer.

25. The composition of claim 23, further comprising a vector comprising the nucleotide sequence encoding angiostatin protein, wherein the vector is capable of expressing angiostatin protein when present in a cell.

26. The composition of claim 25, wherein the vector is present in the cell.

* * * * *

UNITED STATES PATENT AND TRADEMARK OFFICE

CERTIFICATE OF CORRECTION

PATENT NO. : 5,792,845

DATED : August 11, 1998

INVENTOR(S) : Michael S. O'Reilly and M. Judah Folkman

It is certified that error appears in the above-identified patent and that said Letters Patent is hereby corrected as shown below:

column 1, line 2:

"This invention was made with government support under National Institutes of Health grant P01-CA45548. The United States Government may have certain rights in this invention."

Claim 1, line 4, please delete "plaminocen" and insert therefor --plasminogen--.
Claim 10, line 4, please delete "anziostatin" and insert therefor --angiostatin--.

Signed and Sealed this

Twenty-fourth Day of November, 1998

Attest:

BRUCE LEHMAN

*Attesting Officer*

*Commissioner of Patents and Trademarks*